US010610132B2

(12) United States Patent
Gunderson et al.

(10) Patent No.: US 10,610,132 B2
(45) Date of Patent: Apr. 7, 2020

(54) STEP DETECTION USING ACCELEROMETER AXIS

(71) Applicant: Medtronic, Inc., Minneapolis, MN (US)

(72) Inventors: Bruce D. Gunderson, Plymouth, MN (US); Ya-Jian Cheng, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 337 days.

(21) Appl. No.: 15/603,776

(22) Filed: May 24, 2017

(65) Prior Publication Data

US 2018/0035920 A1 Feb. 8, 2018

Related U.S. Application Data

(60) Provisional application No. 62/370,102, filed on Aug. 2, 2016.

(51) Int. Cl.
*A61B 5/07* (2006.01)
*A61B 5/11* (2006.01)
(Continued)

(52) U.S. Cl.
CPC .............. *A61B 5/112* (2013.01); *A61B 5/076* (2013.01); *A61B 5/1121* (2013.01);
(Continued)

(58) Field of Classification Search
CPC .... A61B 5/11; A61B 5/00; A61B 5/07; A61B 5/076; A61B 5/112; A61B 5/1121;
(Continued)

(56) References Cited

U.S. PATENT DOCUMENTS

| 4,374,382 A | 2/1983 | Markowitz |
|---|---|---|
| 5,117,824 A | 6/1992 | Keimel et al. |

(Continued)

FOREIGN PATENT DOCUMENTS

| WO | 2002067449 A2 | 8/2002 |
|---|---|---|
| WO | 2007033194 A2 | 3/2007 |
| WO | 2014083538 A1 | 6/2014 |

OTHER PUBLICATIONS (PCT/US2017/041701) PCT Notification of Transmittal of the International Search Report and the Written Opinion of the International Searching Authority, or the Declaration, dated Oct. 18, 2017, 14 pages.

(Continued)

*Primary Examiner* — Eric J Messersmith
(74) *Attorney, Agent, or Firm* — Shumaker & Sieffert, P.A.

(57) ABSTRACT

Examples described herein include a medical device system comprising an accelerometer circuitry configured to output a signal indicative of variations in accelerations along a single axis of movement of patient; and processing circuitry configured to receive the output signal from the accelerometer, and to rectify the output signal to generate a rectified signal, wherein rectification of the output signal comprises generating a rectified value for each of a plurality of moving windows imposed over the output signal, wherein generating the rectification value for each of the plurality of moving windows comprises determining a current value of the output signal for the window, determining a maximum value for a portion of the output signal enclosed by the window, and subtracting the current value from the maximum value; and analyze the rectified signal to detect the occurrence of a step taken by a patient based on the rectified signal.

20 Claims, 18 Drawing Sheets

(51) Int. Cl.
*A61B 5/00* (2006.01)
*A61N 1/37* (2006.01)
(52) U.S. Cl.
CPC ............ *A61B 5/1126* (2013.01); *A61B 5/686* (2013.01); *A61B 5/7278* (2013.01); *A61B 5/1118* (2013.01); *A61B 2562/0219* (2013.01); *A61N 1/3702* (2013.01)
(58) Field of Classification Search
CPC ..... A61B 5/1126; A61B 5/7278; A61B 5/686; A61B 2562/0219; A61B 5/1118; A61B 5/1123; A61B 5/1116; A61N 1/3702; G01C 22/006; A63B 2220/17; G06K 9/00348
See application file for complete search history.

(56) References Cited

U.S. PATENT DOCUMENTS

| | | | |
|---|---|---|---|
| 5,545,186 | A | 8/1996 | Olson et al. |
| 5,755,736 | A | 5/1998 | Gillberg et al. |
| 6,102,874 | A | 8/2000 | Stone et al. |
| 6,104,949 | A | 8/2000 | Pitts Crick et al. |
| 6,572,557 | B2 | 6/2003 | Tchou et al. |
| 6,719,701 | B2 | 4/2004 | Lade |
| 7,141,026 | B2 | 11/2006 | Aminian et al. |
| 7,149,584 | B1 | 12/2006 | Koh et al. |
| 7,177,684 | B1 | 2/2007 | Kroll et al. |
| 8,206,325 | B1 | 6/2012 | Najafi et al. |
| 8,255,046 | B2 | 8/2012 | Sarkar et al. |
| 8,491,504 | B2 | 7/2013 | Hirth |
| 8,744,572 | B1 | 6/2014 | Greenhut et al. |
| 8,818,505 | B2 | 8/2014 | Bhunia et al. |
| 8,990,041 | B2 | 3/2015 | Grabiner et al. |
| 9,403,000 | B2 | 8/2016 | Lyons et al. |
| 10,264,997 | B1* | 4/2019 | Romrell ................ A61B 5/1118 |
| 10,335,047 | B2 | 7/2019 | Gunderson |
| 2002/0115939 | A1 | 8/2002 | Mulligan et al. |
| 2003/0212445 | A1 | 11/2003 | Weinberg |
| 2004/0015197 | A1 | 1/2004 | Gunderson |
| 2004/0112151 | A1 | 6/2004 | Maxwell et al. |
| 2006/0030892 | A1 | 2/2006 | Kadhiresan et al. |
| 2006/0276848 | A1 | 12/2006 | Min et al. |
| 2007/0021678 | A1 | 1/2007 | Beck et al. |
| 2007/0067005 | A1 | 3/2007 | Schatz et al. |
| 2008/0255626 | A1 | 10/2008 | Fricke et al. |
| 2008/0281550 | A1 | 11/2008 | Hogle et al. |
| 2009/0312649 | A1 | 12/2009 | Lian et al. |
| 2010/0010361 | A1 | 1/2010 | Boute et al. |
| 2010/0030090 | A1 | 2/2010 | Zhang et al. |
| 2010/0030292 | A1 | 2/2010 | Sarkar et al. |
| 2010/0087745 | A1 | 4/2010 | Fischell et al. |
| 2010/0210975 | A1* | 8/2010 | Anthony, III ........ A61B 5/0002 600/595 |
| 2011/0040572 | A1 | 2/2011 | Chmiel et al. |
| 2011/0077865 | A1 | 3/2011 | Chen et al. |
| 2011/0082350 | A1 | 4/2011 | Koh |
| 2011/0106201 | A1 | 5/2011 | Bhunia |
| 2011/0148400 | A1 | 6/2011 | Doerr et al. |
| 2011/0172545 | A1 | 7/2011 | Grudic et al. |
| 2012/0083705 | A1 | 4/2012 | Yuen et al. |
| 2012/0109237 | A1 | 5/2012 | Xiao et al. |
| 2013/0079861 | A1 | 3/2013 | Reinert et al. |
| 2013/0085677 | A1 | 4/2013 | Modi et al. |
| 2013/0123684 | A1 | 5/2013 | Giuffrida et al. |
| 2013/0304414 | A1* | 11/2013 | Levy ................... G01C 22/006 702/141 |
| 2014/0128778 | A1 | 5/2014 | Chan et al. |
| 2014/0276928 | A1 | 9/2014 | Vanderpool et al. |
| 2014/0330172 | A1 | 11/2014 | Jovanov et al. |
| 2014/0358193 | A1 | 12/2014 | Lyons et al. |
| 2014/0364769 | A1 | 12/2014 | Chang et al. |
| 2015/0185044 | A1* | 7/2015 | Nie ..................... G01C 22/006 702/160 |
| 2015/0286285 | A1* | 10/2015 | Pantelopoulos ..... A61B 5/6802 345/156 |
| 2015/0342540 | A1 | 12/2015 | An et al. |
| 2016/0038093 | A1 | 2/2016 | Sharma et al. |
| 2016/0045140 | A1* | 2/2016 | Kitamura .............. A61B 5/1116 600/595 |
| 2016/0100776 | A1 | 4/2016 | Najafi et al. |
| 2016/0155313 | A1 | 6/2016 | Chang et al. |
| 2016/0209232 | A1 | 7/2016 | Yang et al. |
| 2016/0220153 | A1 | 8/2016 | Annegam et al. |
| 2017/0067933 | A1* | 3/2017 | Miller .................... G01P 21/00 |
| 2017/0188897 | A1* | 7/2017 | Thein .................. A61B 5/7221 |
| 2017/0344919 | A1 | 11/2017 | Chang et al. |
| 2018/0035898 | A1 | 2/2018 | Gunderson |
| 2018/0035920 | A1 | 2/2018 | Gunderson et al. |
| 2018/0035924 | A1 | 2/2018 | Gunderson et al. |
| 2018/0035956 | A1 | 2/2018 | Gunderson et al. |

OTHER PUBLICATIONS (PCT/US2017/041621) PCT Notification of Transmittal of the International Search Report and the Written Opinion of the International Searching Authority, or the Declaration, dated Oct. 27, 2017, 14 pages.
Giuberti et al., "Automatic UPDRS Evaluation in the Sit-to-Stand Task of Parkinsonians: Kinetic Analysis and Comparative Outlook on the Leg Agility Task", IEEE Journal of Biomedical and Health Informatics, May 2015, pp. 2168-2194, vol. 19, No. 3.
Veltink, et al., "Detection of Static and Dynamic Activities Using Uniaxial Accelerometers", IEEE Transacations on Rehabilitation Engineering, Dec. 1996, pp. 1063-6528, vol. 4, No. 4.
Wieling et al., "Testing for Autonomic Neuropathy: Heart Rate Changes After Orthostatic Manoeuvers and Static Muscle Contractions," Clinical Science (London), 1983, pp. 581-586, vol. 64, No. 6.
(PCT/US2017/041451) PCT Notification of Transmittal of the International Search Report and the Written Opinion of the International Searching Authority, or the Declaration, dated Sep. 21, 2017, 14 pages.
(PCT/US2017/041483) PCT Notification of Transmittal of the International Search Report and the Written Opinion of the International Searching Authority, or the Declaration, dated Sep. 25, 2017, 14 pages.
(PCT/US2017/041713) PCT Notification of Transmittal of the International Search Report and the Written Opinion of the International Searching Authority, or the Declaration, dated Sep. 27, 2017, 14 pages.
Alberts et al., "Using Accelerometer and Gyroscopic Measures to Quantify Postural Stability," Journal of Athletic Training, vol. 50, No. 6, Jun. 2015, 11 pp.
Barde, "What to use to express the variability of data: Standard deviation or standard error of mean?," Perspectives in clinical Research, Jul. 2012, 5 pp.
Chang et al., "A Wireless Accelerometer-Based Body Posture Stability Detection System and Its Application for Meditation Practitioners," Sensors, ISSN: 1424-8220, Dec. 18, 2012, 13 pp.
Hubble et al., "Wearable Sensor Use for Assessing Standing Balance and Walking Stability in People with Parkinson's Disease: A Systematic Review," Plos One, Apr. 20, 2015, 22 pp.
Rigoberto et al., "Postural sway parameters using a triaxial accelerometer: Comparing elderly and young healthy adults," Computer Methods in Biomechanics and Biomedical Engineering, Feb. 21, 2011, 12 pp.
U.S. Appl. No. 16/552,925, filed Aug. 27, 2019 by Gunderson et al.

* cited by examiner

STEP DETECTION USING ACCELEROMETER AXIS

RELATED APPLICATIONS

This application claims the benefit of U.S. Provisional Application No. 62/370,102, filed Aug. 2, 2016, incorporated by reference herein.

FIELD

The disclosure relates generally to medical device systems and, more particularly, medical device system configured to detect and count steps taken by a person or a patient coupled with the medical device system.

BACKGROUND

Implantable medical devices (IMDs) and external, e.g., wearable, medical devices, including implantable pacemakers and implantable cardioverter-defibrillators (ICDs), record cardiac electrogram (EGM) signals for sensing cardiac events, e.g., P-waves and R-waves. IMDs detect episodes of bradycardia, tachycardia and/or fibrillation from the sensed cardiac events, and respond to the episodes as needed with pacing therapy or high-voltage anti-tachyarrhythmia shocks, e.g., cardioversion or defibrillation shocks. Some IMDs include, or are or part of a system that includes, sensors that generate other physiological signals, such as signals that vary based on patient movement or activity, cardiovascular pressure, blood oxygen saturation, edema, or thoracic impedance. Physiological parameters determined based on such signals may be used to assist in the detection of arrhythmia, as well as the detection or monitoring of other cardiac conditions, such as heart failure or infarction, or, more generally, well-being of the patient.

SUMMARY

In general, this disclosure is directed to techniques for detecting steps taken by a person or patient coupled to a medical device, and to record the detected steps, for example using a counter. Coupling a person or a patient to the medical device in some examples includes implantation of the medical device within the body of the patient, or in other examples coupling may comprise fastening the medical device externally to but in contact with the person or patient, for example in the form of a wearable medical device. In various examples, the medical device is configured to provide an output signal generated from a single axis accelerometer located within or coupled to the person or patient. The output signal generated form the single axis accelerometer is processed according to the various techniques described herein to generate a "rectified signal." The "rectified signal" is then analyzed to determine when the person or patient has made a movement that is determined to be a qualifying step, for example when walking or running. In various examples, detection of a qualifying step is made based on the rectified signal being compared to an auto-adjusting threshold value. In various examples, detected qualifying steps are recorded in a counter that is configured to keep track of a total number of detected qualifying steps over various parameters, such as over time, or over a predefined event, such as a distance walked or run by the person or patient coupled to the medical device.

As one example, the disclosure is directed to medical device system comprising: an accelerometer circuitry configured to output a signal indicative of variations in accelerations along a single axis of movement of patient; and processing circuitry configured to: receive the output signal from the accelerometer, and to rectify the output signal to generate a rectified signal, wherein rectification of the output signal comprises generating a rectified value for each of a plurality of moving windows imposed over the output signal, wherein generating the rectification value for each of the plurality of moving windows comprises determining a current value of the output signal for the window, determining a maximum value for a portion of the output signal enclosed by the window, and subtracting the current value from the maximum value; and analyze the rectified signal to detect the occurrence of a step taken by a patient based on the rectified signal.

As another example, the disclosure is directed to a method comprising: receiving a signal generated as an output signal from a single axis of an accelerometer; rectifying, using a rectifier circuit, the output signal to generate a rectified signal, wherein rectifying the output signal comprises generating a rectified value for each of a plurality of moving windows imposed over the output signal by determining a current value of the output signal for the window, determining a maximum value for a portion of the output signal enclosed by the window, and subtracting the current value from the maximum value; and analyzing, using a step sensor circuit, the rectified signal to detect the occurrence of a step taken by a patient coupled to the accelerometer.

In an additional example, the disclosure is directed to a step detection and tracking system comprising an implantable medical device, the implantable medical device comprising an accelerometer circuitry configured to output a signal indicative of variations in accelerations along a single axis of movement of patient; and processing circuitry configured to: receive the output signal from the accelerometer, and to rectify the output signal to generate a rectified signal, wherein rectification of the output signal comprises generating a rectified value for each of a plurality of moving windows imposed over the output signal, wherein generating the rectification value for each of the plurality of moving windows comprises determining a current value of the output signal for the window, determining a maximum value for a portion of the output signal enclosed by the window, and subtracting the current value from the maximum value, and analyze the rectified signal to detect the occurrence of a step taken by a patient based on the rectified signal; and an external device communicatively coupled to the implantable medical device, the external device comprising a display having at least one display field configured to display an indication of a number of steps detected by the implantable medical device.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

Figure 1:
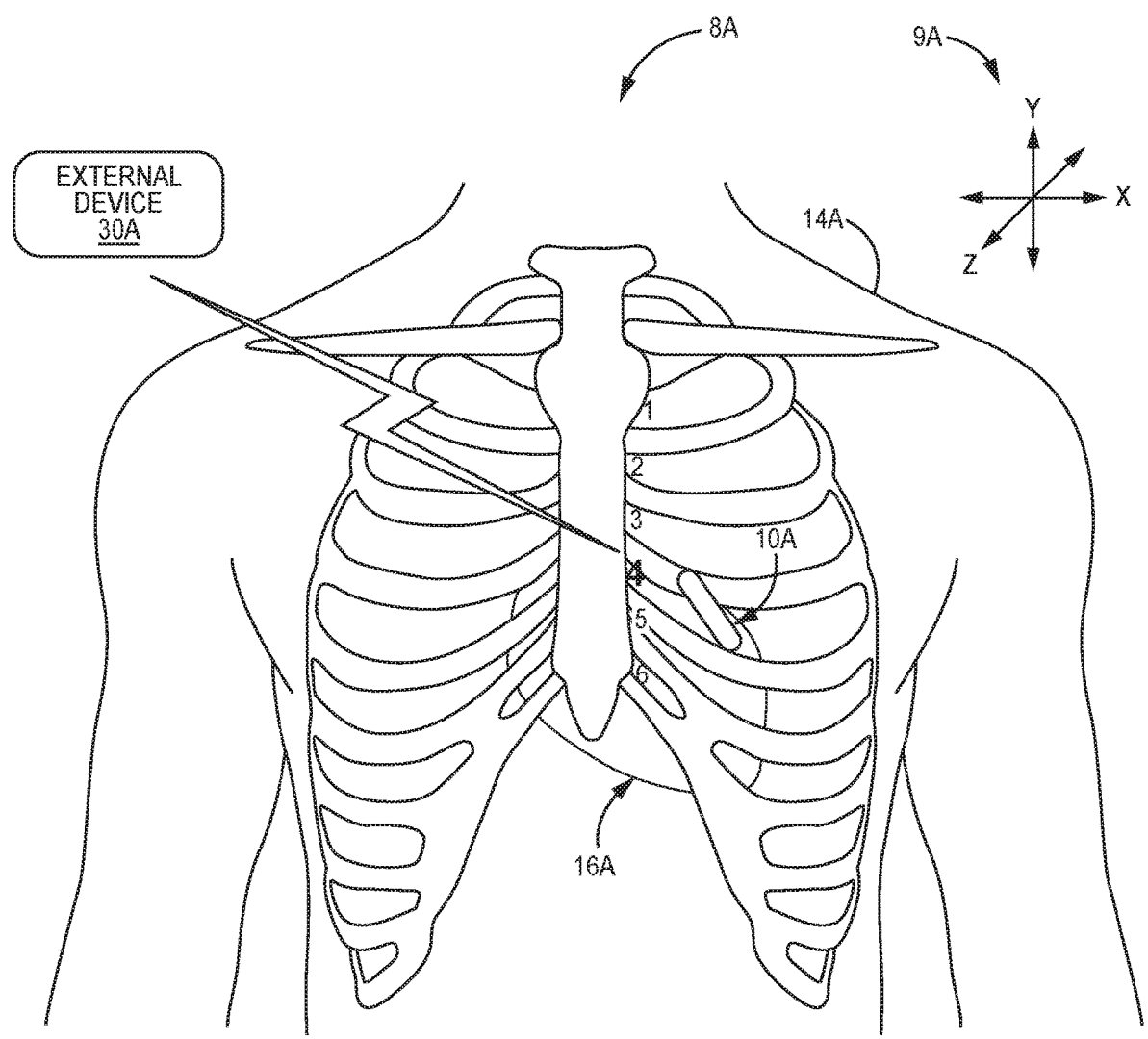
FIG. 1 is a conceptual drawing illustrating an example medical device system in conjunction with a patient.

The drawings and the description provided herein illustrate and describe various examples of the inventive methods, devices, and systems of the present disclosure. However, the methods, devices, and systems of the present disclosure are not limited to the specific examples as illustrated and described herein, and other examples and variations of the methods, devices, and systems of the present disclosure, as would be understood by one of ordinary skill in the art, are contemplated as being within the scope of the present application.

DETAILED DESCRIPTION

Patients that receive implantable devices may benefit from the monitoring their activity. Recent interest in improving health for the general public includes external devices that count steps. If it's true that whatever you measure provides motivation, people may be walking more by being motivated to do by the ability to monitor the number of step they walk and or run. However, these external devices have disadvantages such as falling off, the need for frequent battery charging, not being suitable to be worn in wet environments, etc. An implantable device with a step detector would not have these disadvantages and may provide motivation to a patient having an implantable medical device to improve their level of activity. The ability to monitor activity such as a number of steps taken helps a patient and care providers, such as doctors and nurses, to track progress of therapy determined to be a part of a patient's treatment or recovery process. In many instances, power consumption and the amount of processing required to perform a given function or to provide a feature using an implantable medical device are important considerations in view of size constraints and the limits of stored power available at any given time onboard the implantable medical devices. This disclosure describes example devices and methods that are configured to detect and track steps taken by a patient coupled to an implantable medical device, for example when the implantable medical device is implanted within the patient's body. However, the devices described herein may also be devices that are coupled to the patient without being implanted within the patient's body, for example using devices configured as wearable medical devices, for example but not limited to wearable wristbands, wearable ankle bands, devices fastened to the trunk portion of a patient's body, or other forms of wearable devices such as a shirt.

In various examples, the implantable medical device requires use of only one accelerometer axis to provide a signal that is further processed to detect steps taken by the patient coupled to the implantable medical device. By requiring only a single axis accelerometer input in order to detect patient steps, this feature can be provided by the implantable medical device and require low level of battery/power resources, and also requires a small quantity of devices and electrical circuitry, thus requiring only a small amount of space within the device. In many instances, an implantable medical device already includes one or more accelerometers for monitoring purposes associated with other features provided by the device. As such, the output from an existing accelerometer may be used to provide the signal that is analyzed by the algorithms described herein to detect and track steps taken by the patent.

In various examples, after receiving the output signal generated by a single axis accelerometer provided within the implantable medical device, processing circuitry implementing an algorithm, as further described herein, creates a "rectified signal" that accentuates the peak-to-peak amplitude of the output signal, the "rectification" using a moving window and calculating a difference value between the maximum value within a given moving window and the current value within the moving window. A set of these calculated difference values calculated for a series of these windows is used to generate the "rectified signal." The rectified signal is analyzed using an auto-adjusting threshold, wherein the value of the auto-adjusting threshold in comparison to the value of the "rectified signal" at any given time and over a period of time identifies each step taken by the patient coupled to the implantable medical device. In various examples, detected steps are used to increment a step counter that stores a value indicative of the number of detected steps. In some examples, the value stored in the step counter includes steps detected over a period of time (e.g., over a day, a week, or a year), or during the course of a predefined event, such as the patient going for a walk, or steps taken during a therapy session.

In various examples, the processing circuitry only increments the step counter only when a qualifying step has occurred. In some examples, to be a qualifying step a detected step must have occurred after an initial sequence of steps occurs within an expected speed (e.g., three steps have occurred in sequence at a rate within 30-180 steps/minute). The qualifications for detected steps helps prevent under and over counting of steps, for example when a patent merely shift with from one foot to anther but is not in fact walking, or for example when the patient only moves a minimum number of steps, such as taking one step and then stopping.

A step detector algorithm is described using only a single axis, in some examples the z-axis, of a three-dimensional accelerometer. Various examples of the method utilizing the algorithm to detect steps include receiving the signal generated by the single axis of the three-dimensional accelerometer, rectifying the signal to accentuate the peak-to-peak amplitudes present in the received signal, and to automatically adjust a threshold value at each maximum amplitude following a period when the rectified signal returns to a zero-baseline value. In various examples the received signal is filtered using a low pass filter before being rectified, the filtering process configured to remove high frequency nose from the signal. In various examples, the method includes incrementing a step courter after some number of consecutive steps are detected that fall between a particular range of steps per minute.

FIG. 1 is a conceptual drawing illustrating an example medical device system 8A in conjunction with a patient 14A. Medical device system 8A is an example of a medical device system configured to implement the techniques described herein for detecting steps taken by the patient 14A. In the illustrated example, medical device system 8A includes an IMD 10A and an external device 30A.

IMD 10A is an insertable cardiac monitor (ICM) capable of sensing and recording cardiac EGM signals from a position outside of heart 16A, and will be referred to as ICM 10A hereafter. In some examples, ICM 10A includes or is coupled to one or more additional sensors that generate one or more other physiological signals, such as signals that vary based on patient motion and/or posture, blood flow, or respiration. Additional sensors included in ICM 10A comprise at least one single axis accelerometer, and in various examples may include a plurality of single axis accelerometers, one or more multiple-axis accelerometers, and some combination of single axis and multiple axis accelerometers. ICM 10A may be implanted outside of the thorax of patient 14A, e.g., subcutaneously or submuscularly, such as the pectoral location illustrated in FIG. 1. In some examples, ICM 10A may take the form of a Reveal LINQ™ ICM, available from Medtronic plc, of Dublin, Ireland.

ICM 10A may transmit EGM signal data and other physiological parameter data collected by ICM 10A to an external device 30A. External device 30A may be a computing device, e.g., used in a home, ambulatory, clinic, or hospital setting, to communicate with ICM 10A via wireless telemetry. External device 30A may be coupled to a remote patient monitoring system, such as Carelink®, available from Medtronic plc, of Dublin, Ireland. External device 30A may be, as examples, a programmer, external monitor, or consumer device, e.g., smart phone.

External device 30A may be used to program commands or operating parameters into ICM 10A for controlling its functioning, e.g., when configured as a programmer for ICM 10A. External device 30A may be used to interrogate ICM 10A to retrieve data, including device operational data as well as physiological data accumulated in IMD memory. The interrogation may be automatic, e.g., according to a schedule, or in response to a remote or local user command. Programmers, external monitors, and consumer devices are examples of external devices 30A that may be used to interrogate ICM 10A. Examples of communication techniques used by ICM 10A and external device 30A include radiofrequency (RF) telemetry, which may be an RF link established via Bluetooth, WiFi, or medical implant communication service (MICS).

Both ICM 10A and external device 30A include processing circuitry, and the processing circuitry of either or both device may perform the techniques described herein, such as receiving a sensed waveform representative of an output signal generated by an axis of a single axis or multiple-axis accelerometer included within ICM 10A, and to process that output signal to perform detection of one or more qualifying steps taken by the patient 14A.

Accelerometers included within ICM 10A comprise one more accelerometers configured to measure acceleration forces along one or more of the axis shown with respect to coordinate system 9A in FIG. 1. A "X" axis of coordinate system 9A lies along an axis running horizontally between the left side and right side of patient 14A, a "Y" axis of coordinate system 9A lies along an axis running vertically in a direction from the head to the feet of patient 14A, and a "Z" axis of coordinate system 9A lies along an axis running horizontally between the front and back sides of patient 14A. In various examples, the devices and techniques disclosed herein are configured to receive an output signal generated by an accelerometer measuring accelerations along a single axis of acceleration, and to process the output signal to provide step detection based on the single axis accelerometer output signal as describe herein. In various examples, the axis selected for using in generating the output signal to detect steps according to the techniques as disclosed herein is an accelerometer oriented along the "Z" axis and configured to provide an output signal generated in response to acceleration forces generated along a sagittal plane of patient 14A.

ICM 10A is an example of a device that may include one or more accelerometers and processing circuitry, as further described below, configured to receive a signal axis accelerometer output signal, to process the output signal, to rectify the signal, and to process the rectified signal to detect whether steps, such as when walking or running, have been made by patient 14A. In various examples, ICM 10A, external device 30A, or both ICM 10A and external device 30A are configured to include one or more counters configured to store and track a number of steps detected by the processing circuitry.

Figure 2:
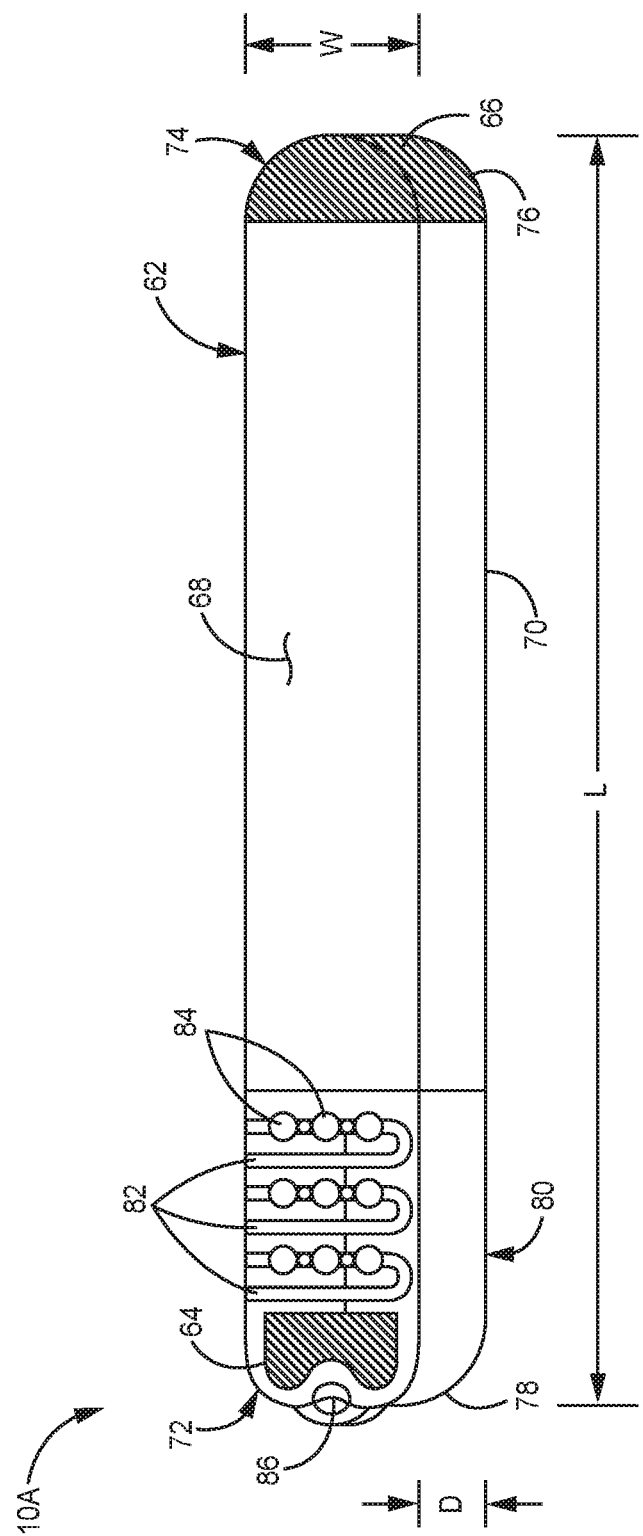
FIG. 2 is a conceptual drawing illustrating another example configuration of the medical device system of FIG. 1.

FIG. 2 is a conceptual drawing illustrating another example configuration of ICM 10A. In the example shown in FIG. 2, ICM 10A may be embodied as a monitoring device having housing 62, proximal electrode 64 and distal electrode 66. Housing 62 may further comprise first major surface 68, second major surface 70, proximal end 72, and distal end 74. Housing 62 encloses electronic circuitry located inside the ICM 10A and protects the circuitry contained therein from body fluids. Electrical feedthroughs provide electrical connection of electrodes 64 and 66.

In the example shown in FIG. 2, ICM 10A is defined by a length L, a width W and thickness or depth D and is in the form of an elongated rectangular prism wherein the length L is much larger than the width W, which in turn is larger than the depth D. In one example, the geometry of the ICM 10A—in particular a width W greater than the depth D—is selected to allow ICM 10A to be inserted under the skin of the patient using a minimally invasive procedure and to remain in the desired orientation during insertion. For example, the device shown in FIG. 2 includes radial asymmetries (notably, the rectangular shape) along the longitudinal axis that maintains the device in the proper orientation following insertion. For example, in one example the spacing between proximal electrode 64 and distal electrode 66 may range from 30 millimeters (mm) to 55 mm, 35 mm to 55 mm, and from 40 mm to 55 mm and may be any range or individual spacing from 25 mm to 60 mm. In addition, ICM 10A may have a length L that ranges from 30 mm to about 70 mm. In other examples, the length L may range from 40 mm to 60 mm, 45 mm to 60 mm and may be any length or range of lengths between about 30 mm and about 70 mm. In addition, the width W of major surface 68 may range from 3 mm to 10 mm and may be any single or range of widths between 3 mm and 10 mm. The thickness of depth D of ICM 10A may range from 2 mm to 9 mm. In other examples, the depth D of ICM 10A may range from 2 mm to 5 mm and may be any single or range of depths from 2 mm to 9 mm. In addition, ICM 10A according to an example of the present disclosure is has a geometry and size designed for ease of implant and patient comfort. Examples of ICM 10A described in this disclosure may have a volume of three cubic centimeters (cm) or less, 1.5 cubic cm or less or any volume between three and 1.5 cubic centimeters.

In the example shown in FIG. 2, once inserted within the patient, the first major surface 68 faces outward, toward the skin of the patient while the second major surface 70 is located opposite the first major surface 68. When implanted, the first major surface 68 and the second major surface 70 line in separate and parallel planes that are substantially perpendicular to a z-axis of the patient, such as the z-axis of coordinate axis system 9A as shown in FIG. 1. As illustrated in FIG. 2, the depth dimension D of ICM 10A lies along a same dimension as the z-axis, and in various examples is a sagittal axis of the patient once ICM 10A is implanted in a patient. ICM 10A may include an accelerometer that provides a single axis accelerometer output signal indicative of variations in the acceleration forces present in this z-axis relative to the patient into which the ICM 10A device is implanted. The single axis accelerometer output may be used to detect steps taken by the patient having the implanted ICM 10A device, such as when the patient is walking or running. In addition, in the example shown in FIG. 2, proximal end 72 and distal end 74 are rounded to reduce discomfort and irritation to surrounding tissue once inserted under the skin of the patient. ICM 10A, including instrument and method for inserting ICM 10A is described, for example, in U.S. Patent Publication No. 2014/0276928, incorporated herein by reference in its entirety.

Proximal electrode 64 and distal electrode 66 are used to sense cardiac signals, e.g. ECG signals, intra-thoracically or extra-thoracically, which may be sub-muscularly or subcutaneously. ECG signals may be stored in a memory of the ICM 10A, and ECG data may be transmitted via integrated antenna 82 to another medical device, which may be another implantable device or an external device, such as external device 30A. In some example, electrodes 64 and 66 may additionally or alternatively be used for sensing any biopotential signal of interest, which may be, for example, an EGM, EEG, EMG, or a nerve signal, from any implanted location.

In the example shown in FIG. 2, proximal electrode 64 is in close proximity to the proximal end 72 and distal electrode 66 is in close proximity to distal end 74. In this example, distal electrode 66 is not limited to a flattened, outward facing surface, but may extend from first major surface 68 around rounded edges 76 and/or end surface 78 and onto the second major surface 70 so that the electrode 66 has a three-dimensional curved configuration. In the example shown in FIG. 2, proximal electrode 64 is located on first major surface 68 and is substantially flat, outward facing. However, in other examples proximal electrode 64 may utilize the three-dimensional curved configuration of distal electrode 66, providing a three-dimensional proximal electrode (not shown in this example). Similarly, in other examples distal electrode 66 may utilize a substantially flat, outward facing electrode located on first major surface 68 similar to that shown with respect to proximal electrode 64. The various electrode configurations allow for configurations in which proximal electrode 64 and distal electrode 66 are located on both first major surface 68 and second major surface 70. In other configurations, such as that shown in FIG. 2, only one of proximal electrode 64 and distal electrode 66 is located on both major surfaces 68 and 70, and in still other configurations both proximal electrode 64 and distal electrode 66 are located on one of the first major surface 68 or the second major surface 70 (i.e., proximal electrode 64 located on first major surface 68 while distal electrode 66 is located on second major surface 70). In another example, ICM 10A may include electrodes on both major surface 68 and 70 at or near the proximal and distal ends of the device, such that a total of four electrodes are included on ICM 10A. Electrodes 64 and 66 may be formed of a plurality of different types of biocompatible conductive material, e.g. stainless steel, titanium, platinum, iridium, or alloys thereof, and may utilize one or more coatings such as titanium nitride or fractal titanium nitride.

In the example shown in FIG. 2, proximal end 72 includes a header assembly 80 that includes one or more of proximal electrode 64, integrated antenna 82, anti-migration projections 84, and/or suture hole 86. Integrated antenna 82 is located on the same major surface (i.e., first major surface 68) as proximal electrode 64 and is also included as part of header assembly 80. Integrated antenna 82 allows ICM 10A to transmit and/or receive data. In other examples, integrated antenna 82 may be formed on the opposite major surface as proximal electrode 64, or may be incorporated within the housing 82 of ICM 10A. In the example shown in FIG. 2, anti-migration projections 84 are located adjacent to integrated antenna 82 and protrude away from first major surface 68 to prevent longitudinal movement of the device. In the example shown in FIG. 2, anti-migration projections 84 includes a plurality (e.g., nine) small bumps or protrusions extending away from first major surface 68. As discussed above, in other examples anti-migration projections 84 may be located on the opposite major surface as proximal electrode 64 and/or integrated antenna 82. In addition, in the example shown in FIG. 2 header assembly 80 includes suture hole 86, which provides another means of securing ICM 10A to the patient to prevent movement following insert. In the example shown, suture hole 86 is located adjacent to proximal electrode 64. In one example, header assembly 80 is a molded header assembly made from a polymeric or plastic material, which may be integrated or separable from the main portion of ICM 10A.

ICM 10A is as illustrated and as described above with respect to FIG. 2 includes examples of a device that may include one or more accelerometers and processing circuitry, as further described below, configured to receive a signal axis accelerometer output signal, to process the output signal, to rectify the signal, and to process the rectified signal to detect whether steps, such as when walking or running, have been made by patient 14A.

Figure 3:
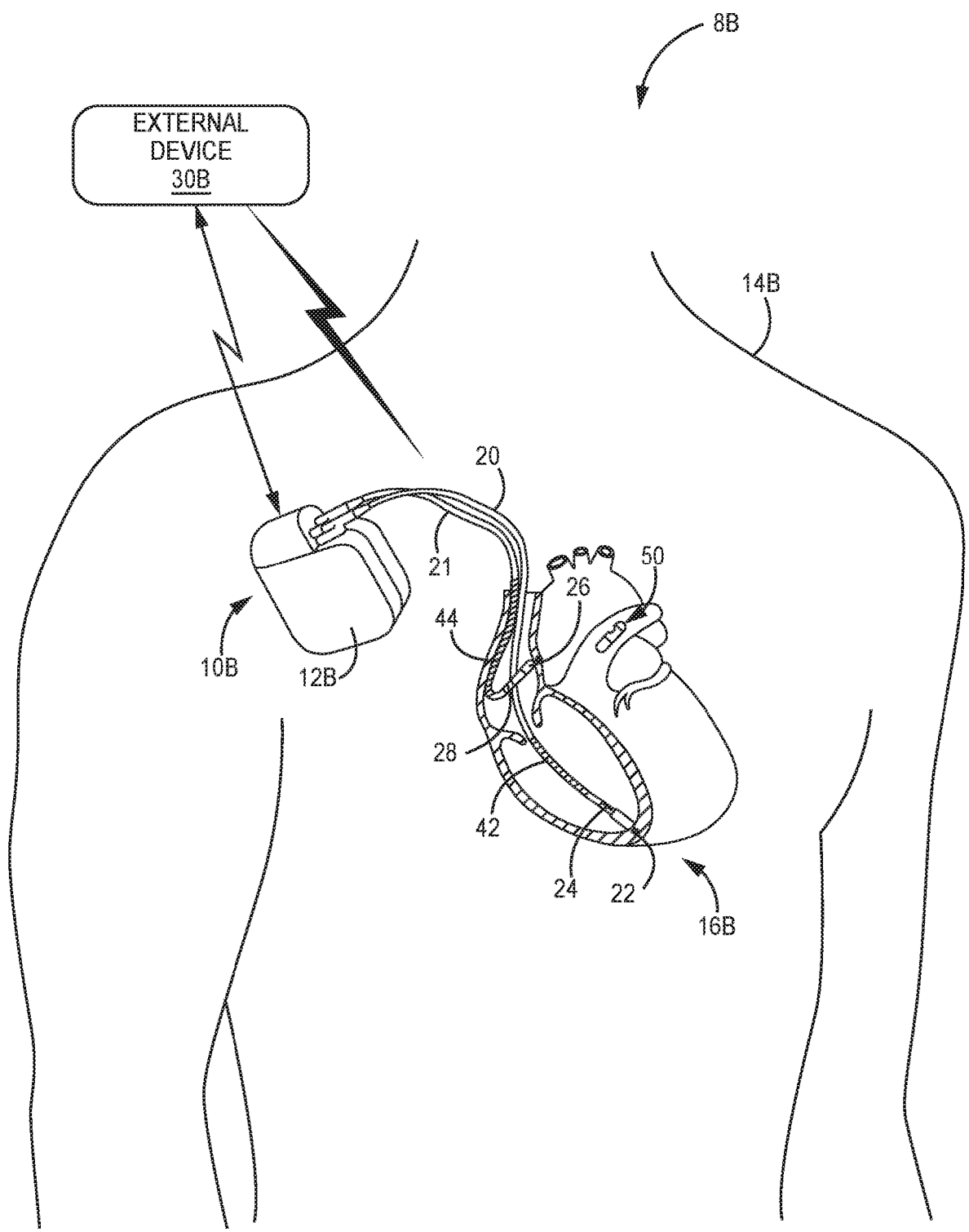
FIG. 3 is a conceptual drawing illustrating an example medical device system in conjunction with a patient.

FIG. 3 is a conceptual drawing illustrating an example medical device system 8B in conjunction with a patient 14B. Medical device system 8B is an example of a medical device system configured to implement the techniques described herein for detecting steps taken by the patient 14B. In the illustrated example, medical device system 8B includes an implantable medical device (IMD) 10B coupled to a ventricular lead 20 and an atrial lead 21. IMB 10B is an implantable cardioverter-defibrillator (ICD) capable of delivering pacing, cardioversion and defibrillation therapy to the heart 16B of a patient 14B, and will be referred to as ICD 10B hereafter.

Ventricular lead 20 and atrial lead 21 are electrically coupled to ICD 10B and extend into the patient's heart 16B. Ventricular lead 20 includes electrodes 22 and 24 shown positioned on the lead in the patient's right ventricle (RV) for sensing ventricular EGM signals and pacing in the RV. Atrial lead 21 includes electrodes 26 and 28 positioned on the lead in the patient's right atrium (RA) for sensing atrial EGM signals and pacing in the RA.

Ventricular lead 20 additionally carries a high voltage coil electrode 42, and atrial lead 21 carries a high voltage coil electrode 44, used to deliver cardioversion and defibrillation shocks. The term "anti-tachyarrhythmia shock" may be used herein to refer to both cardioversion shocks and defibrillation shocks. In other examples, ventricular lead 20 may carry both of high voltage coil electrodes 42 and 44, or may carry a high voltage coil electrode in addition to those illustrated in the example of FIG. 3.

ICD 10B may use both ventricular lead 20 and atrial lead 21 to acquire cardiac electrogram (EGM) signals from patient 14B and to deliver therapy in response to the acquired data. Medical device system 8B is shown as having a dual chamber ICD configuration, but other examples may include one or more additional leads, such as a coronary sinus lead extending into the right atrium, through the coronary sinus and into a cardiac vein to position electrodes along the left ventricle (LV) for sensing LV EGM signals and delivering pacing pulses to the LV. In other examples, a medical device system may be a single chamber system, or otherwise not include atrial lead 21.

Processing circuitry, sensing circuitry, and other circuitry including one or more accelerometers, configured for performing the techniques described herein are housed within a sealed housing 12. Housing 12 (or a portion thereof) may be conductive so as to serve as an electrode for pacing or sensing or as an active electrode during defibrillation. As such, housing 12 is also referred to herein as "housing electrode" 12.

ICD 10B may transmit EGM signal data and cardiac rhythm episode data acquired by ICD 10B, as well as data regarding delivery of therapy by ICD 10B, to an external device 30B. External device 30B may be a computing device, e.g., used in a home, ambulatory, clinic, or hospital setting, to communicate with ICD 10A via wireless telemetry. External device 30B may be coupled to a remote patient monitoring system, such as Carelink®, available from Medtronic plc, of Dublin, Ireland. External device 30B may be, as examples, a programmer, external monitor, or consumer device, e.g., smart phone.

External device 30B may be used to program commands or operating parameters into ICD 10B for controlling its functioning, e.g., when configured as a programmer for ICD 10B. External device 30B may be used to interrogate ICD 10B to retrieve data, including device operational data as well as physiological data accumulated in IMD memory. The interrogation may be automatic, e.g., according to a schedule, or in response to a remote or local user command. Programmers, external monitors, and consumer devices are examples of external devices 30B that may be used to interrogate ICD 10B. Examples of communication techniques used by ICD 10B and external device 30B include radiofrequency (RF) telemetry, which may be an RF link established via Bluetooth, WiFi, or medical implant communication service (MICS).

ICM 10B is as illustrated and as described above with respect to FIG. 3 includes examples of a device that may include one or more accelerometers and processing circuitry, as further described below, configured to receive a signal axis accelerometer output signal, to process the output signal, to rectify the signal, and to process the rectified signal to detect whether steps, such as when walking or running, have been made by patient 14B.

In various examples, a number of detected qualifying steps are tracked using one or more counters, the one or more counters included in either ICM 10B, or external device 30B, or in some combination of or both ICM 10B and the external device 30B. In various examples, the value or values stored in the one or more counters can be retrieved and provided as an output, such as an output to a display (not shown in FIG. 3) associated with external device 30B for display and viewing of the stored counter value or values.

Figure 4A:
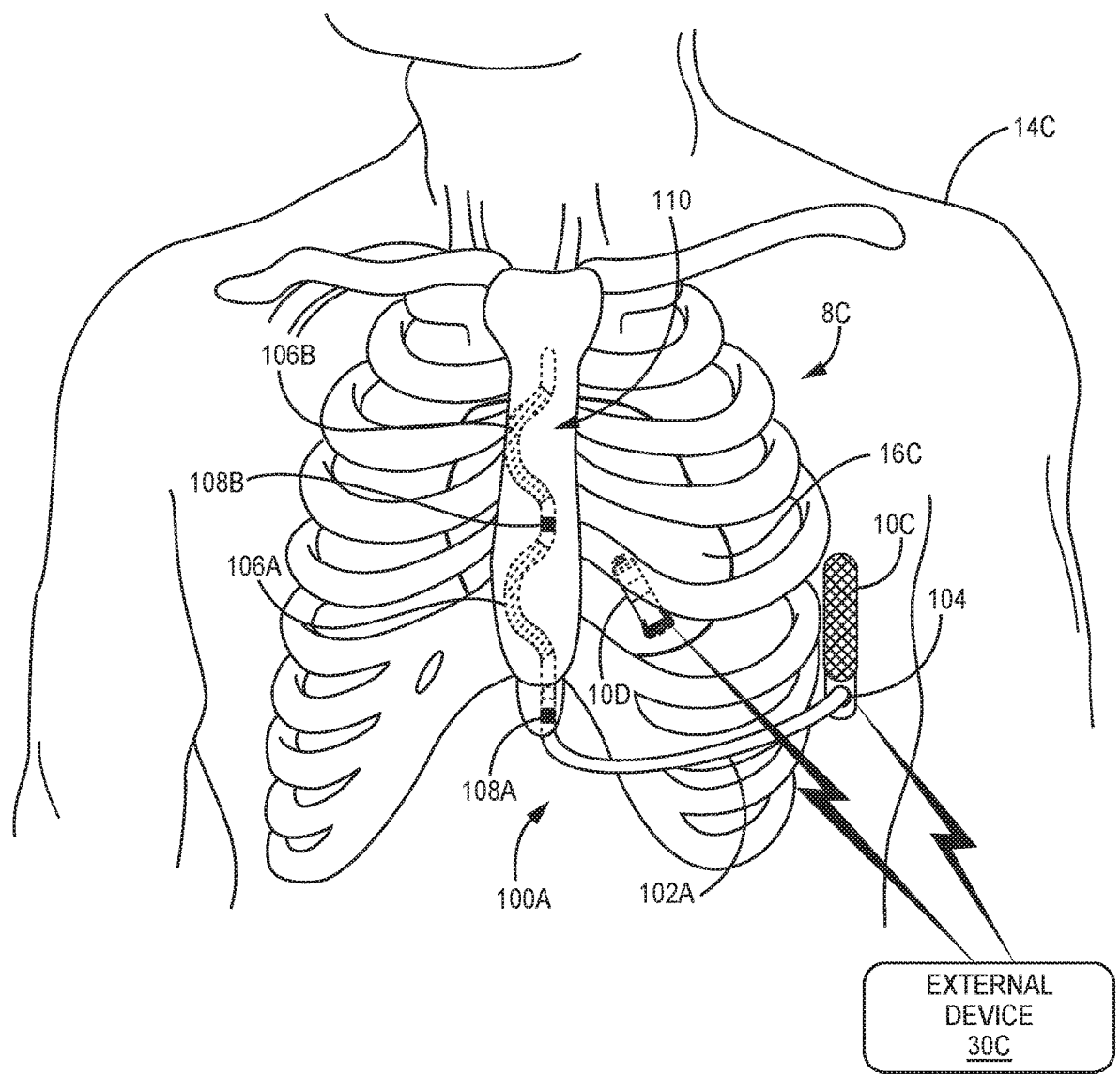
FIGS. 4A-4C are front-view, side-view, and top-view conceptual drawings, respectively, illustrating another example of a medical device system in conjunction with a patient.
Figure 4B:
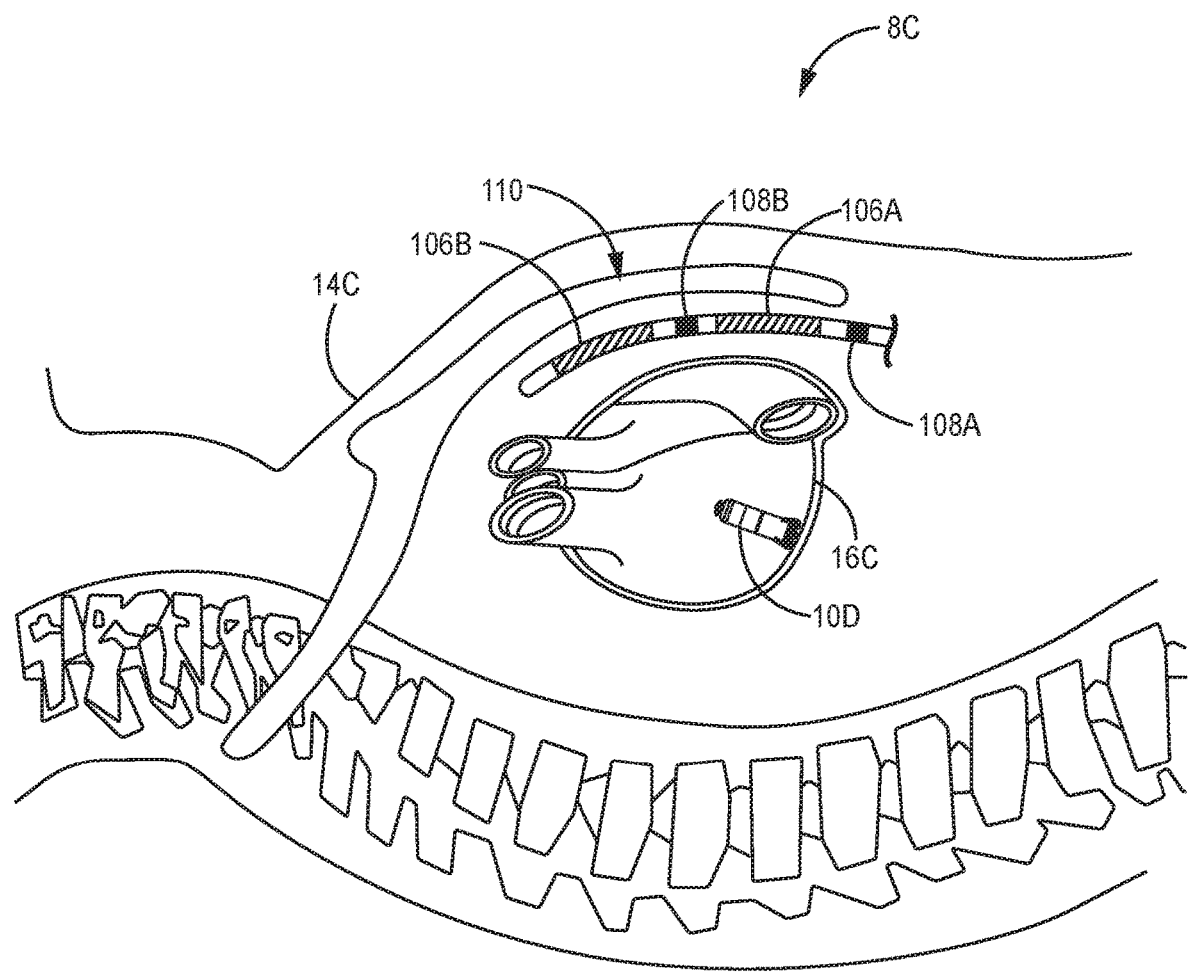
Figure 4C:
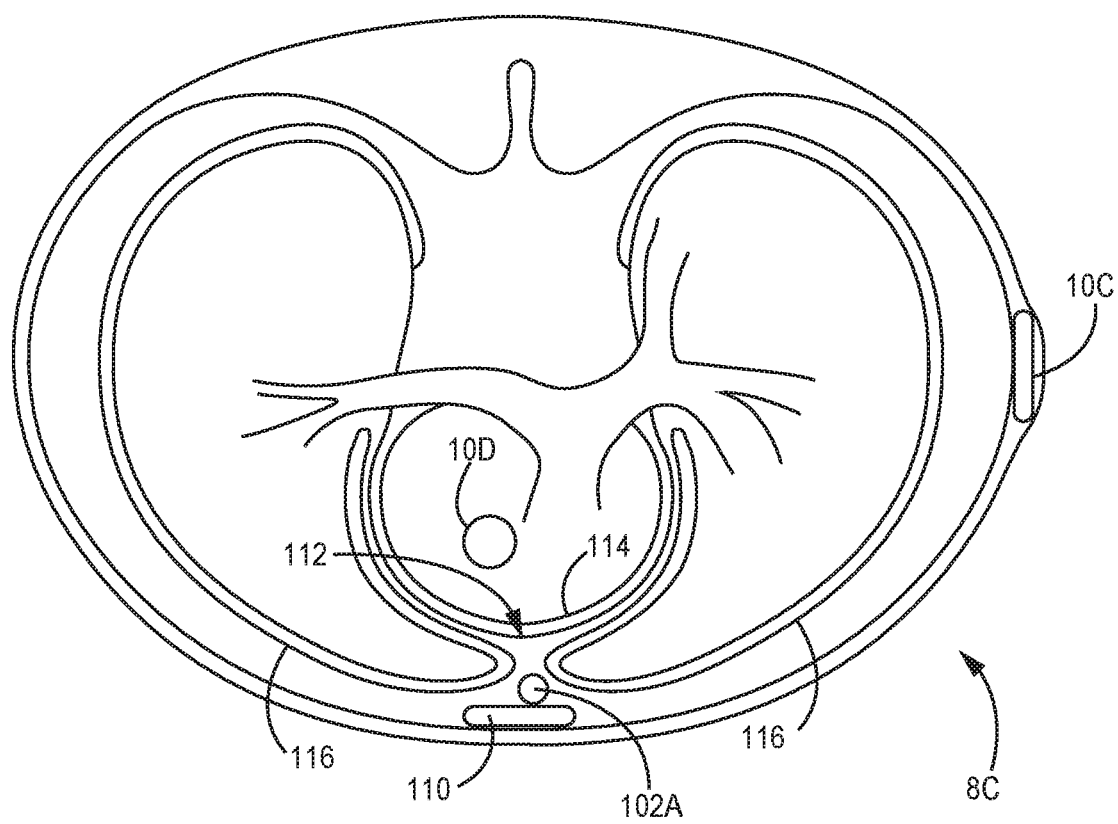

FIGS. 4A-4C are front-view, side-view, and top-view conceptual drawings, respectively, illustrating another example medical device system 8C in conjunction with a patient 14C. Medical device system 8C is another example of a medical device system configured to implement the techniques described herein, such as receiving a sensed waveform representative of an output signal generated by an axis of a single axis or multiple-axis accelerometer included within ICM 10B, and to process that output signal to perform detection of one or more qualifying steps taken by the patient 14A.

In the illustrated example, medical device system 8C includes an extracardiovascular ICD system 100A implanted within a patient 14C. ICD system 100A includes an IMB 10C, which is an ICD and is referred to hereafter as ICD 10C, connected to at least one implantable cardiac defibrillation lead 102A. ICD 10C is configured to deliver high-energy cardioversion or defibrillation pulses to a patient's heart 16C when atrial or ventricular fibrillation is detected. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by ICD 10C.

ICD 10C is implanted subcutaneously or submuscularly on the left side of patient 14C above the ribcage. Defibrillation lead 102A may be implanted at least partially in a substernal location, e.g., between the ribcage and/or sternum 110 and heart 16C. In one such configuration, a proximal portion of lead 102A extends subcutaneously from ICD 10C toward sternum 110 and a distal portion of lead 102A extends superior under or below the sternum 110 in the anterior mediastinum 112 (FIG. 4C). The anterior mediastinum 112 is bounded laterally by the pleurae 116 (FIG. 1C), posteriorly by the pericardium 114 (FIG. 4C), and anteriorly by the sternum 110. In some instances, the anterior wall of the anterior mediastinum may also be formed by the transversus thoracis and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 102A extends along the posterior side of the sternum 110 substantially within the loose connective tissue and/or substernal musculature of the anterior mediastinum. Lead 102A may be at least partially implanted in other intrathoracic locations, e.g., other non-vascular, extra-pericardial locations, including the gap, tissue, or other anatomical features around the perimeter of and adjacent to, but not attached to, the pericardium or other portion of the heart and not above the sternum 110 or ribcage.

In other examples, lead 102A may be implanted at other extracardiovascular locations. For example, defibrillation lead 102A may extend subcutaneously above the ribcage from ICD 10C toward a center of the torso of patient 14C, bend or turn near the center of the torso, and extend subcutaneously superior above the ribcage and/or sternum 110. Defibrillation lead 102A may be offset laterally to the left or the right of the sternum 110 or located over the sternum 110. Defibrillation lead 102A may extend substantially parallel to the sternum 110 or be angled lateral from the sternum 110 at either the proximal or distal end.

Defibrillation lead 102A includes an insulative lead body having a proximal end that includes a connector 104 configured to be connected to ICD 10C and a distal portion that includes one or more electrodes. Defibrillation lead 102A also includes one or more conductors that form an electrically conductive path within the lead body and interconnect the electrical connector and respective ones of the electrodes.

Defibrillation lead 102A includes a defibrillation electrode that includes two sections or segments 106A and 106B, collectively (or alternatively) defibrillation electrode 106. The defibrillation electrode 106 is toward the distal portion of defibrillation lead 102A, e.g., toward the portion of defibrillation lead 102A extending along the sternum 110. Defibrillation lead 102A is placed below and/or along sternum 110 such that a therapy vector between defibrillation electrodes 106A or 106B and a housing electrode formed by or on ICD 10C (or other second electrode of the therapy vector) is substantially across a ventricle of heart 16C. The therapy vector may, in one example, be viewed as a line that extends from a point on defibrillation electrode 106 (e.g., a center of one of the defibrillation electrode sections 106A or 106B) to a point on the housing electrode of ICD 10C. Defibrillation electrode 106 may, in one example, be an elongated coil electrode.

Defibrillation lead 102A may also include one or more sensing electrodes, such as sensing electrodes 108A and 108B (individually or collectively, "sensing electrode(s) 108"), located along the distal portion of defibrillation lead 102A. In the example illustrated in FIG. 4A and FIG. 4B, sensing electrodes 108A and 108B are separated from one another by defibrillation electrode 106A. In other examples, however, sensing electrodes 108A and 108B may be both distal of defibrillation electrode 106 or both proximal of defibrillation electrode 106. In other examples, lead 102A may include more or fewer electrodes at various locations proximal and/or distal to defibrillation electrode 106. In the same or different examples, ICD 10C may include one or more electrodes on another lead (not shown).

ICD system 100A may sense electrical signals via one or more sensing vectors that include combinations of electrodes 108A and 108B and the housing electrode of ICD 10C. In some instances, ICD 10C may sense cardiac electrical signals using a sensing vector that includes one of the defibrillation electrode sections 106A and 106B and one of sensing electrodes 108A and 108B or the housing electrode of ICD 9. The sensed electrical intrinsic signals may include electrical signals generated by cardiac muscle and indicative of depolarizations and repolarizations of heart 16C at various times during the cardiac cycle. ICD 10C analyzes the electrical signals sensed by the one or more sensing vectors to detect tachyarrhythmia, such as ventricular tachycardia or ventricular fibrillation. In response to detecting the tachyarrhythmia, ICD 10C may begin to charge a storage element, such as a bank of one or more capacitors, and, when charged, deliver one or more defibrillation pulses via defibrillation electrode 106 of defibrillation lead 102A if the tachyarrhythmia is still present.

Medical device system 8C also includes an IMD 10D, which is implanted within heart 16C and configured to deliver cardiac pacing to the heart, e.g., is an intracardiac pacing device (IPD). IMD 10D is referred to as IPD 10D hereafter. In the illustrated example, IPD 10D is implanted within the right ventricle of heart 16C. However, in other examples, system 8C may additionally or alternatively include one or more IPDs 10D within other chambers of heart 16C, or similarly configured pacing devices attached to an external surface of heart 16C (e.g., in contact with the epicardium) such that the pacing device is disposed outside of heart 16C.

IPD 10D is configured to sense electrical activity of heart 16C and deliver pacing therapy, e.g., bradycardia pacing therapy, cardiac resynchronization therapy (CRT), anti-tachycardia pacing (ATP) therapy, and/or post-shock pacing, to heart 16C. IPD 10D may be attached to an interior wall of heart 16C via one or more fixation elements that penetrate the tissue. These fixation elements may secure IPD 10D to the cardiac tissue and retain an electrode (e.g., a cathode or an anode) in contact with the cardiac tissue.

IPD 10D may be capable sensing electrical signals using the electrodes carried on the housing of IPD 10D. These electrical signals may be electrical signals generated by cardiac muscle and indicative of depolarizations and repolarizations of heart 16C at various times during the cardiac cycle. IPD 10D may analyze the sensed electrical signals to detect bradycardia and tachyarrhythmias, such as ventricular tachycardia or ventricular fibrillation. In response to detecting bradycardia, IPD 10D may deliver bradycardia pacing via the electrodes of IPD 10D. In response to detecting tachyarrhythmia, IPD 10D may, e.g., depending on the type of tachyarrhythmia, deliver ATP therapy via the electrodes of IPD 10D. In some examples, IPD 10D may deliver post-shock pacing in response to determining that another medical device, e.g., ICD 10C, delivered an anti-tachyarrhythmia shock.

IPD 10D and ICD 10C may be configured to coordinate their arrhythmia detection and treatment activities. In some examples IPD 10D and ICD 10C may be configured to operate completely independently of one another. In such a case, IPD 10D and ICD 10C are not capable of establishing telemetry communication sessions with one another to exchange information about sensing and/or therapy using one-way or two-way communication. Instead, each of IPD 10D and ICD 10C analyze the data sensed via their respective electrodes to make tachyarrhythmia detection and/or therapy decisions. As such, each device does not know if the other will detect the tachyarrhythmia, if or when it will provide therapy, and the like. In some examples, IPD 10D may be configured to detect anti-tachyarrhythmia shocks delivered by ICD system 100A, which may improve the coordination of therapy between subcutaneous ICD 10C and IPD 10D without requiring device-to-device communication. In this manner, IPD 10D may coordinate the delivery of cardiac stimulation therapy, including the termination of ATP and the initiation of the delivery of post-shock pacing, with the application of an anti-tachyarrhythmia shock merely through the detection of defibrillation pulses and without the need to communicate with the defibrillation device applying the anti-tachyarrhythmia shock.

In other examples, IPD 10D and ICD 10C may engage in communication to facilitate the appropriate detection of arrhythmias and/or delivery of therapy. The communication may include one-way communication in which one device is configured to transmit communication messages and the other device is configured to receive those messages. The communication may instead include two-way communication in which each device is configured to transmit and receive communication messages. Two-way communication and coordination of the delivery of patient therapies between IPD 10D and ICD 10C is described in commonly-assigned U.S. patent application Ser. No. 13/756,085, titled, "SYSTEMS AND METHODS FOR LEADLESS PACING AND SHOCK THERAPY," filed Jan. 31, 2013, the entire content of which is incorporated by reference herein.

External device 30C may be configured substantially similarly to external device 30A described above with respect to FIG. 1. External device 30C may be configured to communicate with one or both of ICD 10C and IPD 10D. In examples where external device 30C only communicates with one of ICD 10C and IPD 10D, the non-communicative device may receive instructions from or transmit data to the device in communication with external device 30C. In some examples, a user may interact with device 30C remotely via a networked computing device. The user may interact with external device 30C to communicate with IPD 10D and/or ICD 10C.

For example, the user may interact with external device 30C to send an interrogation request and retrieve sensed physiological data or therapy delivery data stored by one or both of ICD 10C and IPD 10D, and program or update therapy parameters that define therapy, or perform any other activities with respect to ICD 10C and IPD 10D. Although the user is a physician, technician, surgeon, electrophysiologist, or other healthcare professional, the user may be patient 14C in some examples. For example, external device 30C may allow a user to send signals, such as a reset signal, and stop and start signals related to counters provided within IPD 10D, as further described below, to allow user interaction with one or more counters storing values related to a number of detected steps.

Although FIGS. 4A-4C are shown or described in the context of IPD 10D and extracardiovascular ICD system 100A that includes lead 102A with a substernally placed distal portion, techniques in accordance with one or more aspects of the present disclosure may be applicable to other coexistent systems. For example, an extracardiovascular ICD system may include a lead having a distal portion that is implanted subcutaneously above the sternum (or other location) instead of being implanted substernally. As another example, instead of an IPD, a pacing system may be implanted having a pacemaker and one or more leads connected to and extending from the pacemaker into one or more chambers of the heart or attached to the outside of the heart to provide pacing therapy to the one or more chambers. As such, the example of FIGS. 4A-4C is illustrated for example purposes only and should not be considered limiting of the techniques described herein.

Figure 5:
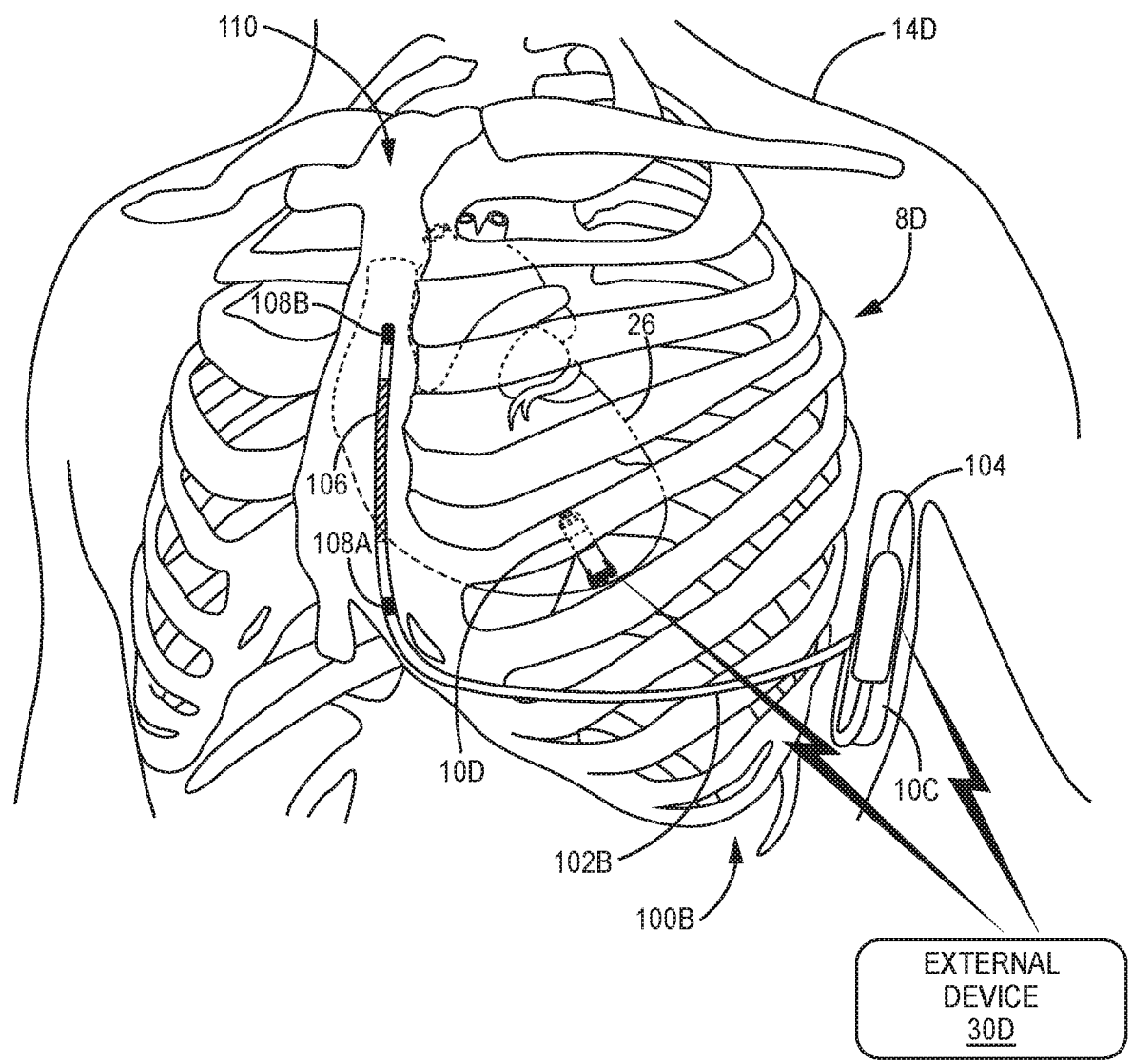
FIG. 5 is a conceptual drawing illustrating another example medical device system in conjunction with a patient.

FIG. 5 is a conceptual drawing illustrating another example medical device system 8D that includes an extracardiovascular ICD system 100B and IPD 10D implanted within a patient. Medical device system 8B may be configured to perform any of the techniques described herein with respect to medical device system 8C of FIGS. 4A-4C. Components with like numbers in FIGS. 4A-4C and FIG. 5 may be similarly configured and provide similar functionality.

In the example of FIG. 5, extracardiovascular ICD system 100B includes ICD 10C coupled to a defibrillation lead 102B. Unlike defibrillation lead 102A of FIGS. 4A-4C, defibrillation lead 102B extends subcutaneously above the ribcage from ICD 10C. In the illustrated example, defibrillation lead 102B extends toward a center of the torso of patient 14D, bends or turns near the center of the torso, and extends subcutaneously superior above the ribcage and/or sternum 110. Defibrillation lead 102B may be offset laterally to the left or the right of sternum 110 or located over sternum 110. Defibrillation lead 102B may extend substantially parallel to sternum 102 or be angled lateral from the sternum at either the proximal or distal end.

Defibrillation lead 102B includes an insulative lead body having a proximal end that includes a connector 104 configured to be connected to ICD 10C and a distal portion that includes one or more electrodes. Defibrillation lead 102B also includes one or more conductors that form an electrically conductive path within the lead body and interconnect the electrical connector and respective ones of the electrodes. In the illustrated example, defibrillation lead 102B includes a single defibrillation electrode 106 toward the distal portion of defibrillation lead 102B, e.g., toward the portion of defibrillation lead 102B extending along sternum 110. Defibrillation lead 102B is placed along sternum 110 such that a therapy vector between defibrillation electrode 106 and a housing electrode formed by or on ICD 10C (or other second electrode of the therapy vector) is substantially across a ventricle of heart 16D.

Defibrillation lead 102B may also include one or more sensing electrodes, such as sensing electrodes 108A and 108B, located along the distal portion of defibrillation lead 102B. In the example illustrated in FIG. 5, sensing electrodes 108A and 108B are separated from one another by defibrillation electrode 106. In other examples, however, sensing electrodes 108A and 108B may be both distal of defibrillation electrode 106 or both proximal of defibrillation electrode 106. In other examples, lead 102B may include more or fewer electrodes at various locations proximal and/or distal to defibrillation electrode 106, and lead 102B may include multiple defibrillation electrodes, e.g., defibrillation electrodes 106A and 106B as illustrated in the example of FIGS. 4A-4C.

Figure 6:
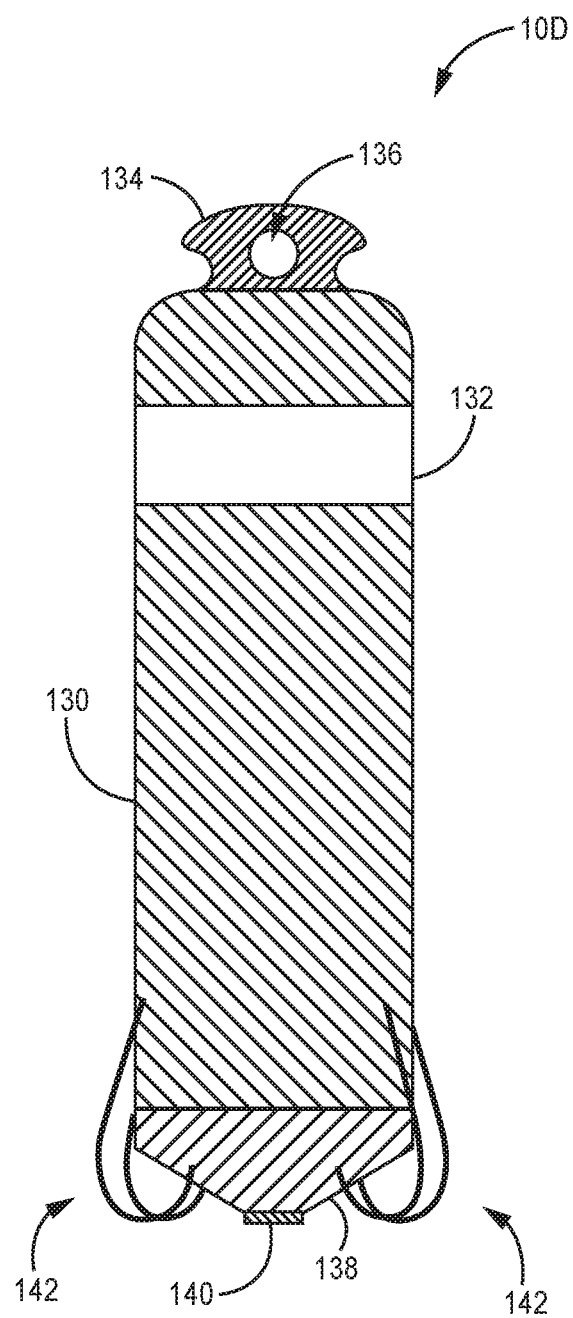
FIG. 6 is a conceptual diagram illustrating an example configuration of the intracardiac pacing device of FIGS. 4A-5.

FIG. 6 is a conceptual drawing illustrating an example configuration of IPD 10D. As shown in FIG. 6, IPD 10D includes case 130, cap 138, electrode 140, electrode 132, fixation mechanisms 142, flange 134, and opening 136. Together, case 130 and cap 138 may be considered the housing of IPD 10D. In this manner, case 130 and cap 138 may enclose and protect the various electrical components, e.g., circuitry, within IPD 10D. Case 130 may enclose substantially all of the electrical components, and cap 138 may seal case 130 and create the hermetically sealed housing of IPD 10D. Although IPD 10D is generally described as including one or more electrodes, IPD 10D may typically include at least two electrodes (e.g., electrodes 132 and 140)

to deliver an electrical signal (e.g., therapy such as cardiac pacing) and/or provide at least one sensing vector.

Electrodes 132 and 140 are carried on the housing created by case 130 and cap 138. In this manner, electrodes 132 and 140 may be considered leadless electrodes. In the example of FIG. 6, electrode 140 is disposed on the exterior surface of cap 138. Electrode 140 may be a circular electrode positioned to contact cardiac tissue upon implantation. Electrode 132 may be a ring or cylindrical electrode disposed on the exterior surface of case 130. Both case 130 and cap 138 may be electrically insulating.

Electrode 140 may be used as a cathode and electrode 132 may be used as an anode, or vice versa, for delivering cardiac pacing such as bradycardia pacing, CRT, ATP, or post-shock pacing. However, electrodes 132 and 140 may be used in any stimulation configuration. In addition, electrodes 132 and 140 may be used to detect intrinsic electrical signals from cardiac muscle.

Fixation mechanisms 142 may attach IPD 10D to cardiac tissue. Fixation mechanisms 142 may be active fixation tines, screws, clamps, adhesive members, or any other mechanisms for attaching a device to tissue. As shown in the example of FIG. 6, fixation mechanisms 142 may be constructed of a memory material, such as a shape memory alloy (e.g., nickel titanium), that retains a preformed shape. During implantation, fixation mechanisms 142 may be flexed forward to pierce tissue and allowed to flex back towards case 130. In this manner, fixation mechanisms 142 may be embedded within the target tissue.

Flange 144 may be provided on one end of case 130 to enable tethering or extraction of IPD 10D. For example, a suture or other device may be inserted around flange 144 and/or through opening 146 and attached to tissue. In this manner, flange 144 may provide a secondary attachment structure to tether or retain IPD 10D within heart 16C (or 16D) if fixation mechanisms 142 fail. Flange 144 and/or opening 146 may also be used to extract IPD 10D once the IPD needs to be explanted (or removed) from patient 14D if such action is deemed necessary.

IPD 10D is one example of a pacing device configured to implement the techniques of this disclosure. However, other implantable medical devices may be used to perform the same or similar functions as IPD 10D. For example, an IPD may include a small housing that carries an electrode, similar to IPD 10D, and be configured to be implanted within a chamber of a heart 16. The IPD may also include one or more relatively short leads configured to place one or more respective additional electrodes at another location within the same chamber of the heart or a different chamber of the heart. In this manner, the housing of the IPD may not carry all of the electrodes used to perform functions described herein with respect to IPD 10D. In other examples, each electrode of the IPD may be carried by one or more leads (e.g., the housing of the IPD may not carry any of the electrodes). In some examples, an IPD or other pacing device may include or be coupled to three or more electrodes, where each electrode may deliver therapy and/or detect intrinsic signals.

In another example, a pacing device may be configured to be implanted external to the heart, e.g., near or attached to the epicardium of the heart. An electrode carried by the housing of the pacing may be placed in contact with the epicardium and/or one or more electrodes of leads coupled to the pacing may be placed in contact with the epicardium at locations sufficient to provide cardiac pacing. In still other examples, a pacing device configured to perform the techniques described herein may be implanted subcutaneously or submuscularly, and connected to one or more intracardiac leads carrying one or more electrodes.

Referring back to FIGS. 4A-5, medical device systems 8C and 8D are examples of medical device systems configured to receive an output signal from generated by a single axis of an accelerometer, and to process the output signal in order to detect steps taken by a patent coupled to the accelerometer, such as when the patient is walking or running. In various examples the techniques used to detect steps includes "rectifying" the output signal using a moving window to generate a series of rectified values that can arranged sequentially in time to provide a rectified signal corresponding to the output signal. The rectified signal is then further processed using an auto-adjusting threshold line to determine what portions of the rectified signal represent steps taken by the patient.

Figure 7:
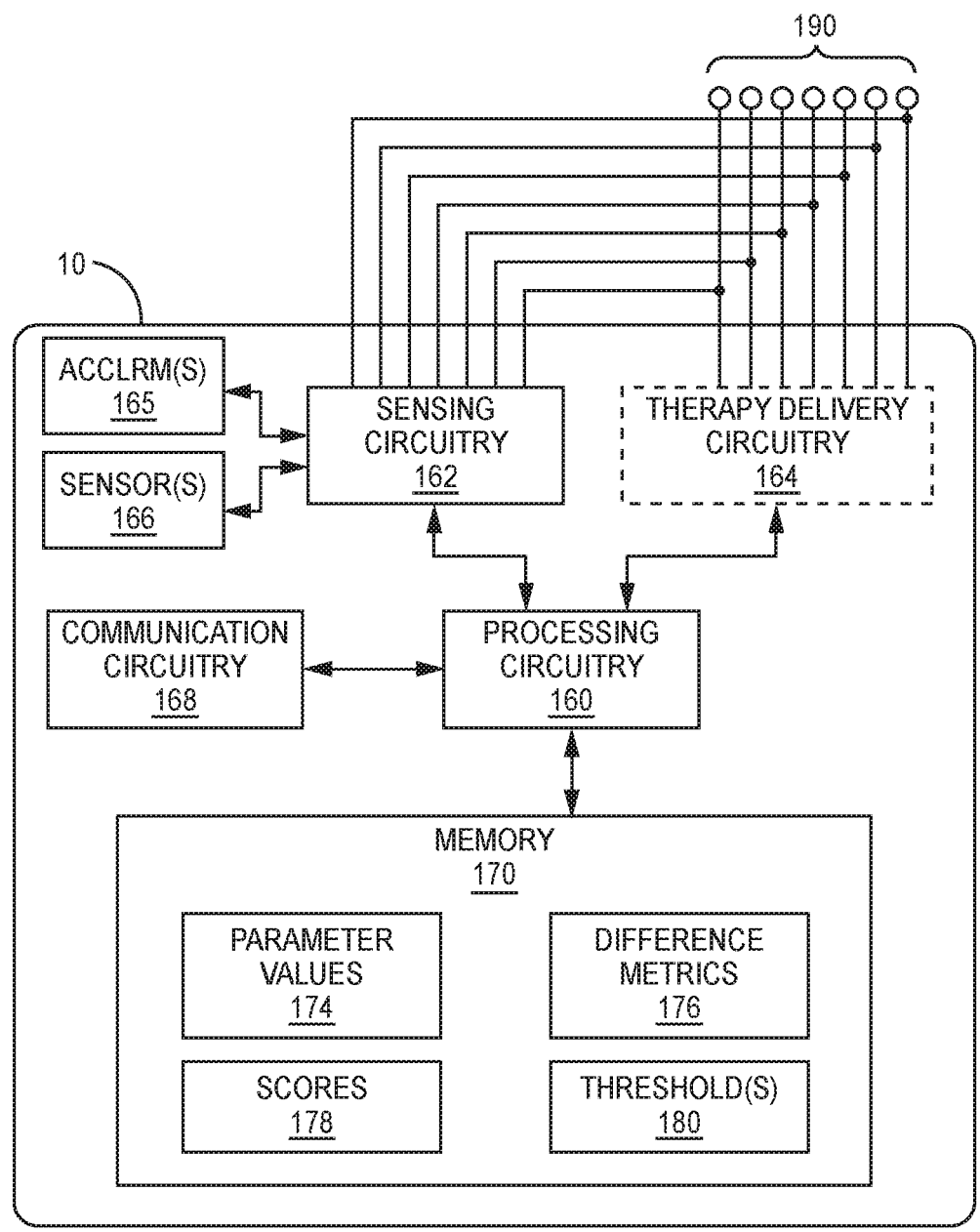
FIG. 7 is a functional block diagram illustrating an example configuration of an implantable medical device.

FIG. 7 is a functional block diagram illustrating an example configuration of an IMD 10. IMD 10 may correspond to any of ICD 10A, ICM 10B, ICD 10C, IPD 10D, or another IMD configured to implement the techniques for predicting an acute cardiac event described in this disclosure. In the illustrated example, IMD 10 includes processing circuitry 160 and an associated memory 170, sensing circuitry 162, therapy delivery circuitry 164, one or more sensors 166, one or more accelerometers 165, and communication circuitry 168. However, ICD 10A, ICM 10B, ICD 10C, and IPD 10D need not include all of these components, or may include additional components. For example, ICM 10A may not include therapy delivery circuitry 164, in some examples. In various examples, processing circuitry 160 is configured to perform the processes of step detection using the one or more of the variations of techniques described herein, including signal processing of a single axis accelerometer output signal, rectification of the single axis output signal, analysis of the rectified signal to provide step detection, and one or more features, including counting and qualification of detected steps according to the techniques described herein. In various examples, an output signal from one axis of the one or more accelerometers 165 is provided as the single axis accelerometer output signal that is process to detect steps taken as represented by the variations present in the accelerometer output signal. In various examples, the output signal from the one axis of the accelerometers 165 is taken from an axis that is oriented in the sagittal axis of the patent once IMD 10 has been implanted in the patient, and provided and output signal indicative of variations in the acceleration forces occurring in that same sagittal axis of the patient.

Memory 170 includes computer-readable instructions that, when executed by processing circuitry 160, cause IMD 10 and processing circuitry 160 to perform various functions attributed to IMD 10 and processing circuitry 160 herein (e.g., determining patient parameter values, difference metrics, scores and thresholds, and determining whether to provide an alert indicating that an acute cardiac event is predicted). Memory 170 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 160 may include fixed function circuitry and/or programmable processing circuitry. Processing circuitry 160 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 160 may include multiple components, such as any combination of one or more microprocessors, one or more controllers, one or more DSPs, one or more ASICs, or one or more FPGAs, as well as other discrete or integrated logic circuitry. The functions attributed to processing circuitry 160 herein may be embodied as software, firmware, hardware or any combination thereof.

Sensing circuitry 162 and therapy delivery circuitry 164 are coupled to electrodes 190. Electrodes 190 illustrated in FIG. 7 may correspond to, for example: electrodes 64 and 66 of ICM 10A (FIG. 1); electrodes 12, 22, 24, 26, 28, 44, and 44 of ICD 10B (FIG. 3); electrodes 106, 108, and one or more housing electrodes of ICD 10C (FIGS. 4A-5); or electrodes 132 and 140 of IPD 10D (FIG. 6).

Electrical sensing circuitry 162 monitors signals from a selected two or more of electrodes 190 in order to monitor electrical activity of heart 26, impedance, or other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 162 may include one or more filters and amplifiers for filtering and amplifying a signal received from electrodes 190.

The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 162 outputs an indication to processing circuitry 160 in response to sensing of a cardiac event (e.g., detected P-waves or R-waves).

In this manner, processing circuitry 160 may receive detected cardiac event signals corresponding to the occurrence of detected R-waves and P-waves in the respective chambers of heart 26. Indications of detected R-waves and P-waves may be used for detecting ventricular and/or atrial tachyarrhythmia episodes, e.g., ventricular or atrial fibrillation episodes. Some detection channels may be configured to detect cardiac events, such as P- or R-waves, and provide indications of the occurrences of such events to processing circuitry 160, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Sensing circuitry 162 may also include a switch module to select which of the available electrodes 190 (or electrode polarities) are used to sense the heart activity. In examples with several electrodes 190, processing circuitry 160 may select the electrodes that function as sense electrodes, i.e., select the sensing configuration, via the switch module within sensing circuitry 162. Sensing circuitry 162 may also pass one or more digitized EGM signals to processing circuitry 160 for analysis, e.g., for use in cardiac rhythm discrimination.

Processing circuitry 160 may implement programmable counters. If IMB 10 is configured to generate and deliver pacing pulses to heart 26, such counters may control the basic time intervals associated with bradycardia pacing (e.g., DDD, VVI, DVI, VDD, AAI, DDI, DDDR, VVIR, DVIR, VDDR, AAIR, DDIR pacing) and other modes of pacing. Intervals defined by processing circuitry 160 may include atrial and ventricular pacing escape intervals, refractory periods during which sensed P-waves and R-waves are ineffective to restart timing of the escape intervals, and the pulse widths of the pacing pulses. The durations of these intervals may be determined by processing circuitry 160 in response to pacing mode parameters stored in memory 170.

Interval counters implemented by processing circuitry 160 may be reset upon sensing of R-waves and P-waves with detection channels of sensing circuitry 162, or upon the generation of pacing pulses by therapy delivery circuitry 164, and thereby control the basic timing of cardiac pacing functions, including bradycardia pacing, CRT, ATP, or post-shock pacing. The value of the count present in the interval counters when reset by sensed R-waves and P-waves may be used by processing circuitry 160 to measure the durations of R-R intervals, P-P intervals, P-R intervals and R-P intervals, which are measurements that may be stored in memory 170. Processing circuitry 160 may use the count in the interval counters to detect a tachyarrhythmia event, such as atrial fibrillation (AF), atrial tachycardia (AT), VF, or VT. These intervals may also be used to detect the overall heart rate, ventricular contraction rate, and heart rate variability. A portion of memory 170 may be configured as a plurality of recirculating buffers, capable of holding series of measured intervals, which may be analyzed by processing circuitry 160 in response to the occurrence of a pace or sense interrupt to determine whether the patient's heart 26 is presently exhibiting atrial or ventricular tachyarrhythmia.

In some examples, an arrhythmia detection method may include any suitable tachyarrhythmia detection algorithms. In one example, processing circuitry 160 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies, such as those methodologies that utilize timing and morphology of the electrocardiogram, may also be employed by processing circuitry 160 in other examples.

In some examples, processing circuitry 160 may determine that tachyarrhythmia has occurred by identification of shortened R-R (or P-P) interval lengths. Generally, processing circuitry 160 detects tachycardia when the interval length falls below 220 milliseconds and fibrillation when the interval length falls below 180 milliseconds. In other examples, processing circuitry 160 may detect ventricular tachycardia when the interval length falls between 330 milliseconds and ventricular fibrillation when the interval length falls below 240 milliseconds. These interval lengths are merely examples, and a user may define the interval lengths as desired, which may then be stored within memory 170. This interval length may need to be detected for a certain number of consecutive cycles, for a certain percentage of cycles within a running window, or a running average for a certain number of cardiac cycles, as examples. In other examples, additional patient parameters may be used to detect an arrhythmia. For example, processing circuitry 160 may analyze one or more morphology measurements, impedances, or any other physiological measurements to determine that patient 14 is experiencing a tachyarrhythmia.

In addition to detecting and identifying specific types of cardiac events, e.g., cardiac depolarizations, sensing circuitry 162 may also sample the detected intrinsic signals to generate an electrogram or other time-based indication of cardiac events. Sensing circuitry 162 may include an analog-to-digital converter or other circuitry configured to sample and digitize the electrical signal sensed via electrodes 190. Processing circuitry 160 may analyze the digitized signal for a variety of purposes, including morphological identification or confirmation of tachyarrhythmia of heart 26.

In some examples, accelerometer 165 include one or more accelerometers, e.g., one or more 3-axis accelerometers. Signals generated by the one or more accelerometers may be indicative of, as examples, gross body movement (e.g., activity) of patient 14, patient posture, heart sounds or other vibrations or movement associated with the beating of the heart, or coughing, rales, or other respiration abnormalities.

Therapy delivery circuitry 164 is configured to generate and deliver electrical therapy to the heart. Therapy delivery circuitry 164 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 164 may include a first set of components configured to provide pacing therapy and a second set of components configured to provide anti-tachyarrhythmia shock therapy. In other instances, therapy delivery circuitry 164 may utilize the same set of components to provide both pacing and anti-tachyarrhythmia shock therapy. In still other instances, therapy delivery circuitry 164 may share some of the pacing and shock therapy components while using other components solely for pacing or shock delivery.

Therapy delivery circuitry 164 may include charging circuitry, one or more charge storage devices, such as one or more capacitors, and switching circuitry that controls when the capacitor(s) are discharged to electrodes 190 and the widths of pulses. Charging of capacitors to a programmed pulse amplitude and discharging of the capacitors for a programmed pulse width may be performed by therapy delivery circuitry 164 according to control signals received from processing circuitry 160, which are provided by processing circuitry 160 according to parameters stored in memory 170. Processing circuitry 160 controls therapy delivery circuitry 164 to deliver the generated therapy to the heart via one or more combinations of electrodes 190, e.g., according to parameters stored in memory 170. Therapy delivery circuitry 164 may include switch circuitry to select which of the available electrodes 190 are used to deliver the therapy, e.g., as controlled by processing circuitry 160.

Communication circuitry 168 includes any suitable hardware, firmware, software or any combination thereof for communicating with another device, such as an external device 30 or another IMD or sensor. Under the control of processing circuitry 160, communication circuitry 168 may receive downlink telemetry from and send uplink telemetry to external device 30 or another device with the aid of an antenna, which may be internal and/or external. In some examples, communication circuitry 168 may communicate with a local external device, and processing circuitry 160 may communicate with a networked computing device via the local external device and a computer network, such as the Medtronic CareLink® Network developed by Medtronic, plc, of Dublin, Ireland.

A clinician or other user may retrieve data from IMD 10 using external device 30 or another local or networked computing device configured to communicate with processing circuitry 160 via communication circuitry 168. The retrieved data may include one or more counter values stored in counter included in processing circuitry 160 and/or in memory 170, the counter values corresponding to number values for detected steps. The clinician may also program parameters of IMD 10 using external device 30 or another local or networked computing device. In some examples, the clinician may select patient parameters, such as a range of time limits between steps for a given patient in order to have a detected step counted as a "qualifying step, and further described below.

Figure 8:
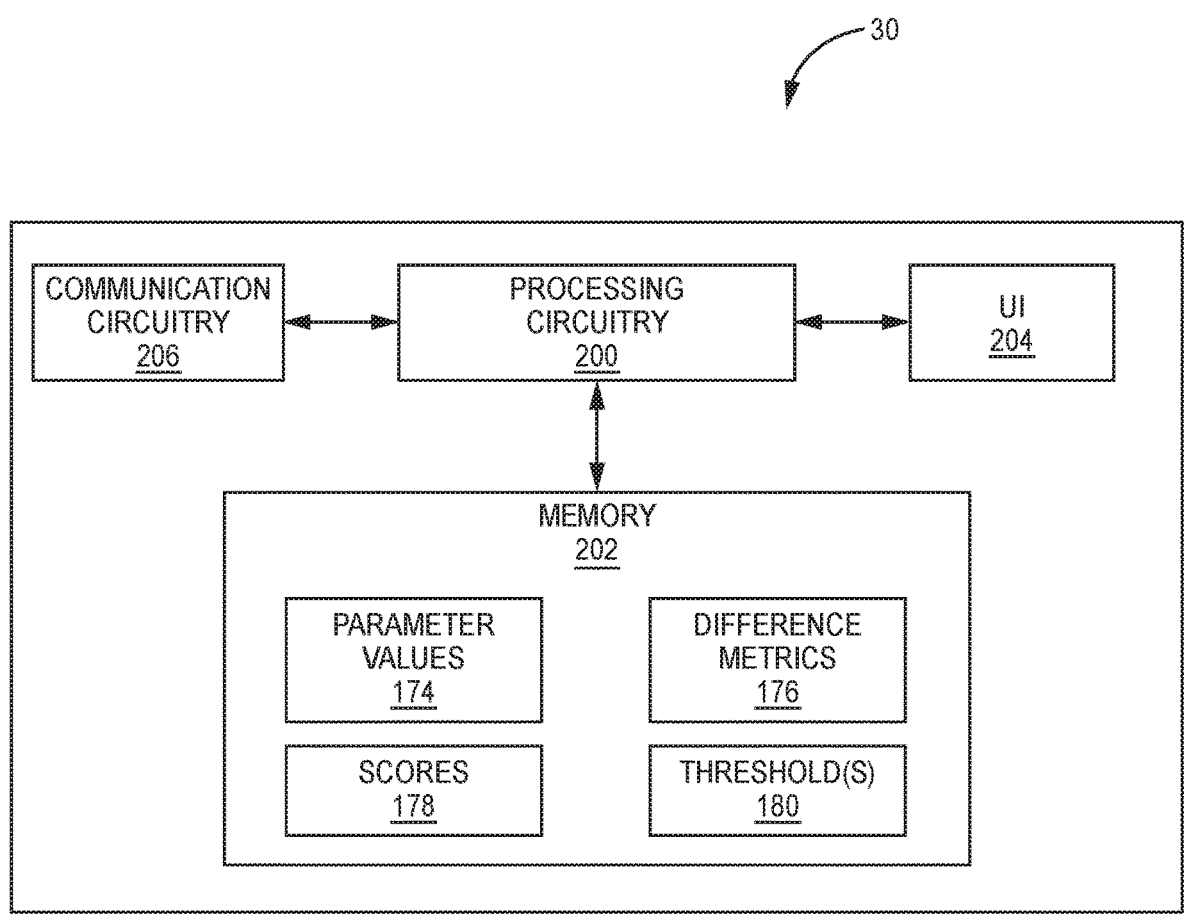
FIG. 8 is a functional block diagram illustrating an example configuration of an external device configured to communicate with one or more implantable medical devices.

FIG. 8 is a functional block diagram illustrating an example configuration of an external device 30 configured to communicate with one or more IMDs 10. In the example of FIG. 8, external device 30 includes processing circuitry 200, memory 202, user interface (UI) 204, and communication circuitry 206. External device 30 may correspond to any of external devices 30A-30C described with respect to FIGS. 1, 2, and 4A-5. External device 30 may be a dedicated hardware device with dedicated software for the programming and/or interrogation of an IMD 10. Alternatively, external device 30 may be an off-the-shelf computing device, e.g., running an application that enables external device 30 to program and/or interrogate IMD 10.

In some examples, a user uses external device 30 to select or program any of the values for operational parameters of IMD 10, e.g., for patient parameter sensing, therapy delivery, and related to the detection of steps. In some examples, a user uses external device 30 to receive data collected by IMD 10, such as step counts or other operational and performance data of IMD 10. The user may interact with external device 30 via UI 204, which may include a display to present a graphical user interface to a user, and a keypad or another mechanism (such as a touch sensitive screen) for receiving input from a user. External device 30 may communicate wirelessly with IMD 10 using communication circuitry 206, which may be configured for RF communication with communication circuitry 168 of IMD 10.

Processing circuitry 200 may include any combination of integrated circuitry, discrete logic circuity, analog circuitry, such as one or more microprocessors, digital signal processors (DSPs), application specific integrated circuits (ASICs), or field-programmable gate arrays (FPGAs). In some examples, processing circuitry 200 may include multiple components, such as any combination of one or more microprocessors, one or more DSPs, one or more ASICs, or one or more FPGAs, as well as other discrete or integrated logic circuitry, and/or analog circuitry.

Memory 202 may store program instructions, which may include one or more program modules, which are executable by processing circuitry 200. When executed by processing circuitry 200, such program instructions may cause processing circuitry 200 and external device 30 to provide the functionality ascribed to them herein. The program instructions may be embodied in software, firmware and/or RAMware. Memory 202 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In some examples, processing circuitry 200 of external device 30 may be configured to provide some or all of the functionality ascribed to processing circuitry 160 of IMD 10 herein. For example, processing circuitry 200 may receive an output signal from a single axis of an accelerometer, and process the output signal to generate rectified values corresponding to the output signal. In various examples, the rectified values are generated using a sequence of moving window imposed over a predetermined number of samples of the output signal. Processing circuitry 200 then arranges these generated rectified values in sequential order over time to generate a rectified signal that have variations corresponding to the variations provided in the output signal. The rectified signal is then analyzed using an auto-adjusting threshold, as further described below, to detect the presence of variation in the rectified signal indicative of a step taken by a patient, such as when a patient is walking or running. In various examples, processing circuity 200 and memory 202 perform any of the functions described above with respect to processing circuity 160 the detection of steps taken by a patient, including the processing of a received single axis accelerometer signal to detect steps, and to provide any of the counter functions described herein related to qualifying and counting detected and/or qualifying steps.

Figure 9:
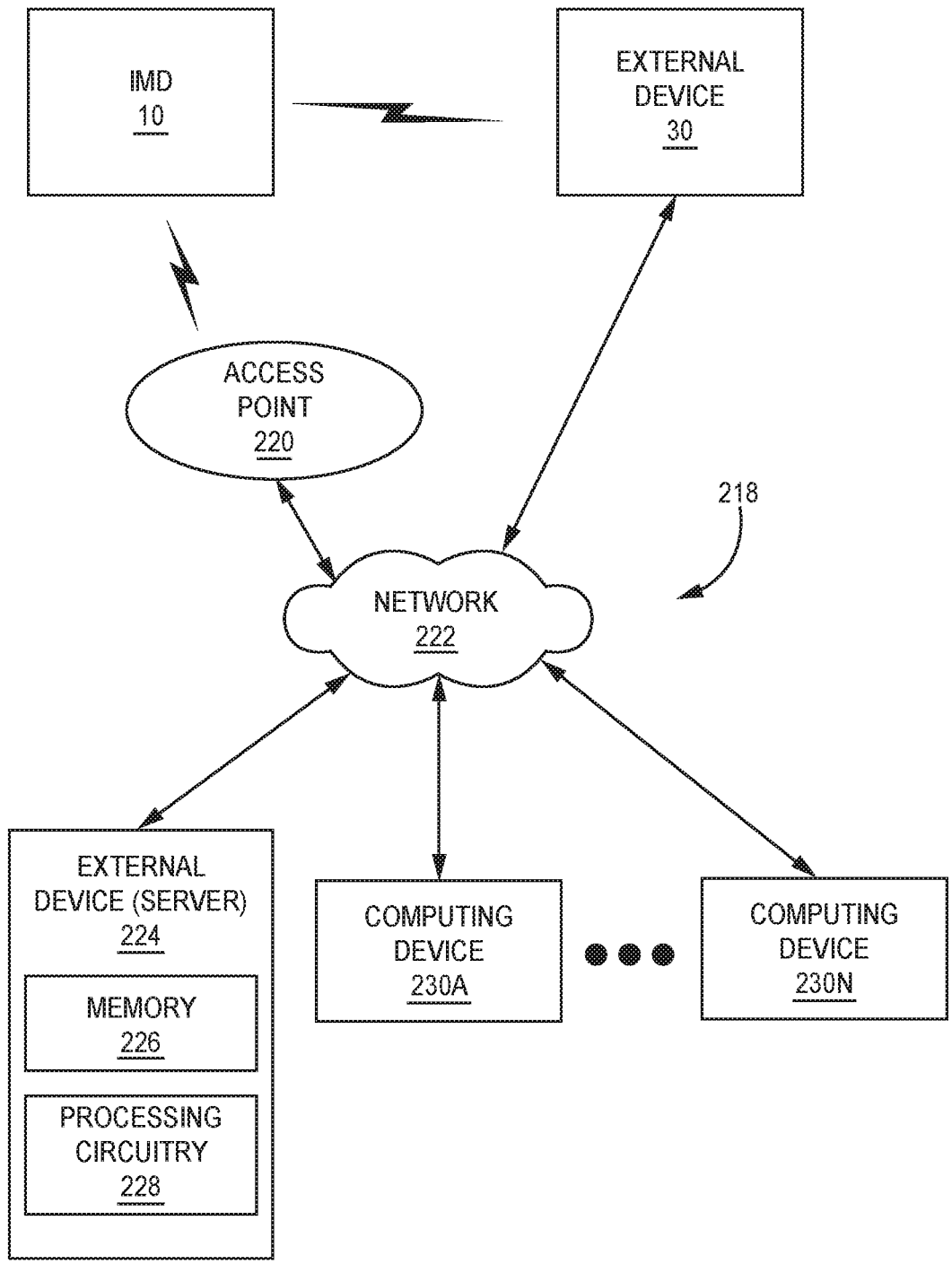
FIG. 9 is a functional block diagram illustrating an example system that includes remote computing devices, such as a server and one or more other computing devices, that are connected to an implantable medical device and/or external device via a network.

FIG. 9 is a functional block diagram illustrating an example system that includes external computing devices, such as a server 224 and one or more other computing devices 230A-230N, that are coupled to IMD 10 and external device 30 via a network 222. In this example, IMD 10 may use its communication module 168 to, e.g., at different times and/or in different locations or settings, communicate with external device 30 via a first wireless connection, and to communication with an access point 220 via a second wireless connection. In the example of FIG. 9, access point 220, external device 30, server 224, and computing devices 230A-230N are interconnected, and able to communicate with each other, through network 222.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with patient 14. Access point 220 may interrogate IMD 10, e.g., periodically or in response to a command from patient 14 or network 222, to retrieve physiological signals, patient parameter values 174, difference metrics 176, scores 178, thresholds 180, alerts of acute cardiac events, and/or other operational or patient data from IMD 10. Access point 220 may provide the retrieved data to server 224 via network 222.

In some cases, server 224 may be configured to provide a secure storage site for data that has been collected from IMD 10 and/or external device 30. In some cases, server 224 may assemble data in web pages or other documents for viewing by trained professionals, such as clinicians, via computing devices 230A-230N. The illustrated system of FIG. 9 may be implemented, in some aspects, with general network technology and functionality similar to that provided by the Medtronic CareLink® Network developed by Medtronic plc, of Dublin, Ireland.

In some examples, one or more of access point 220, server 224, or computing devices 230 may be configured to perform, e.g., may include processing circuitry configured to perform, some or all of the techniques described herein, e.g., with respect to processing circuitry 160 of IMD 10 and processing circuitry 200 of external device 30, related to the detection of steps taken by a patient coupled to an accelerometer, such as when the patient is walking or running. In the example of FIG. 9, server 224 includes a memory 226 to store count values related to detected steps taking by a patent, the count values received from IMD 10 and/or external device 30, and processing circuitry 228, which may be configured to provide some or all of the functionality ascribed to processing circuitry 160 of IMD 10 and processing circuitry 200 of external device 30 herein. For example, processing circuitry 228 may detect steps taken by a patient, determine if the detected step is a qualifying step, and further described herein, and track the number of detected steps using one or more counters. The one or more counters may include a base counter that counts a total number of detected steps until the counter is reset, either by the patient or by another person, such as a clinician, using an external device. In addition, the one or more counters may also include interval counters that can begin counting detected and/or qualifying steps based on a command or signal received by the processing circuit, for example provided by the patient through an external device, and can stop counting detected and/or qualifying steps based on a second or different command or signal provide by the patient through an external device.

Figure 10A:
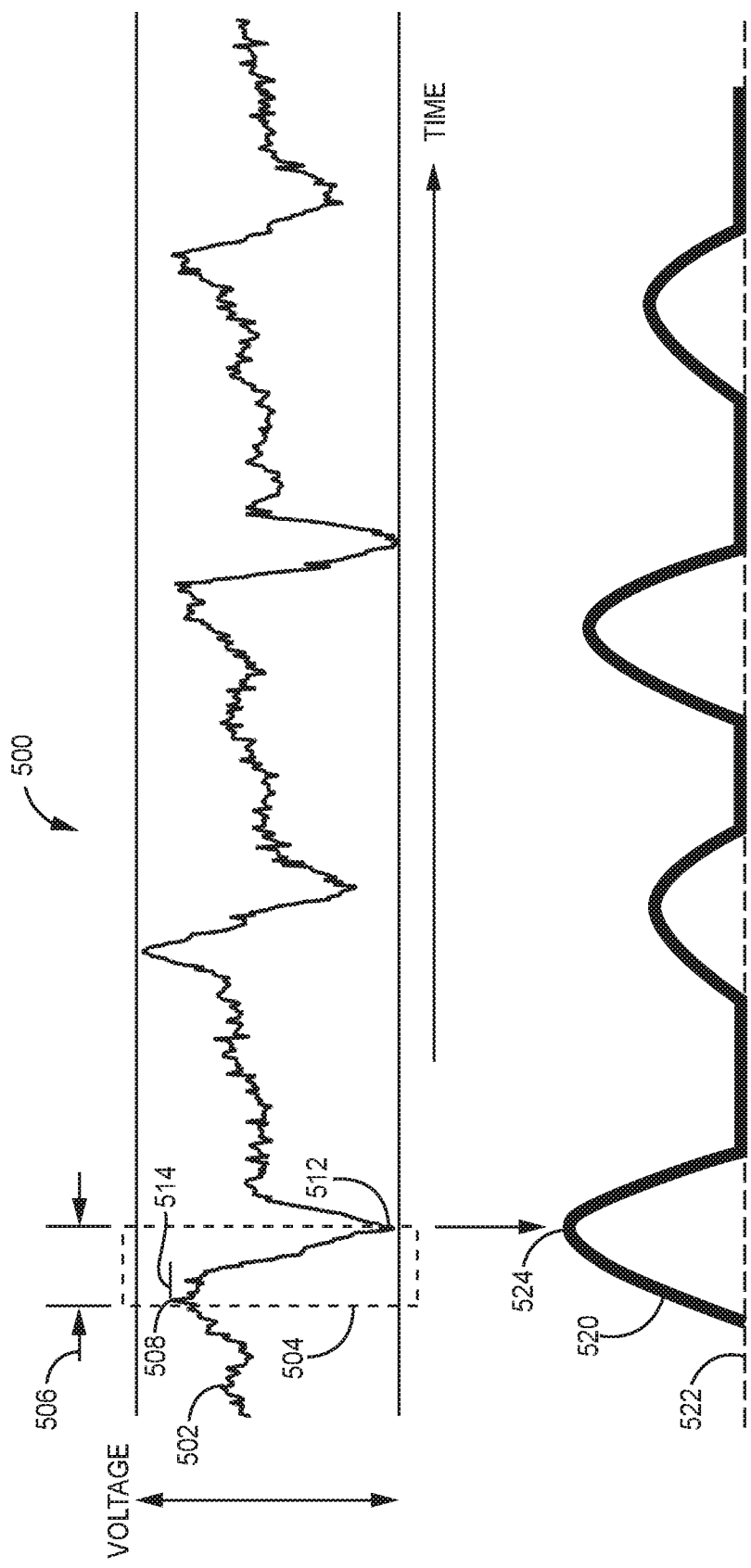
FIG. 10A is a graphical illustration showing rectification of a sensed waveform in accordance with various techniques described in this disclosure.

FIG. 10A is a graphical illustration 500 showing rectification of a sensed waveform in accordance with various techniques described in this disclosure. A sensed waveform 502 is illustrated having a variation in voltage, represented by the vertical axis, relative to time as represented along the horizontal axis. In various examples, sensed waveform 502 is a voltage signal provided as an output signal a single axis accelerometer, such as accelerometer 165 shown in FIG. 7. In various examples, sensed waveform 502 is a voltage output signal provided by a single axis of an accelerometer included in an implanted medical device that is implanted in a patient and arranged so as to provide variations in sensed acceleration along a sagittal axis of the patient. The range of voltage variation provided within sensed waveform 502 is not limited to any particular range of voltage variation, and in some examples is the voltage variation of sensed waveform 502 as provided by the accelerometer configured to generated and provide the single axis accelerometer output signal processed to detect steps. In various examples, instead of the signal 502 showing variations in voltage relative to the vertical axis, the variations are scaled to represent variations in gravitational force, measured in units of gravity—e.g., gravity=9.80991 m/s², and the variations in waveform 502 represent variations, measured in units, in the gravitational forces exerted in the axis being monitored by a single axis accelerometer provided the output signal, or the sampled version of an output signal corresponding to signal 502.

As illustrated in FIG. 10A, sensed waveform 502 is "rectified" to generate a rectified signal 520. As used herein, the term "rectified" is not referring to the classical meaning of "rectification" of a waveform that comprises changing a waveform that includes both positive and negative voltages relative to some reference voltage level into a waveform that includes only positive voltage levels relative to that same reference voltage level. Instead, "rectification" as used herein refers to developing the rectified signal 520 from the sensed waveform 502 using values determined from a set of sample windows, as further described herein, to generate a positive waveform that includes accentuated peak-to-peak amplitudes relative to the peak-to-peak amplitudes provided in the sensed waveform 502. A "positive waveform" in reference to rectified signal 520 comprises a waveform having all values that are either zero or greater than a baseline (zero) value, the baseline value represented by dashed line 522 in FIG. 10A. Accentuation of the peak-to-peak amplitudes of the sensed waveform 502 in the rectified signal 520 makes detection of the steps taken by a patient having the implanted medical device that includes the accelerometer generating the sensed waveform 502 more reliable once the rectified signal 520 is generated and then analyzed to determine the occurrence of steps. The process of analyzing a rectified signal, such as rectified signal 520, to detect steps is further described below with respect to the step detection process.

In various examples, prior to generating the rectified signal 520 from sensed waveform 502, sensed waveform 502 is filtered using a low pass filter to remove higher frequency noise from the signal. In various examples, the low pass filter has a cutoff frequency of 10 Hz. In various examples, the low pass filter has a frequency rolloff of 15 db/10 Hz. However, the cutoff frequency and/or the frequency rolloff for a low pass filter used to filter sensed waveform 502 are not limited to having these particular illustrative values, and other values and combinations of values for the cutoff frequency and frequency rolloff of a low pass filter used to filter waveform 502 are contemplated for filtering of the sensed waveform 502. The type of low pass filter used to filter sensed waveform 502 is not limited to any particular type of filter, and may comprise any type of electronic low pass filter. Examples of electronic low pass filters that may be used to filter the sensed waveform 502 include passive filters, e.g., resistive/capacitive (RC) filters, resistive/inductive (RL) filters, resistive/inductive/capacitive (RLC) filters, and active low pass filters that include active devices such as transistors and/or operational amplifiers. In various examples, the low pass filter used to filter sensed waveform 502 is one of a first order filter, a second order filter, or a higher order filter. In examples where filtering of the sensed waveform 502 is performed, the signal that is "rectified" to generated the rectified signal 520 is the signal generated by the filtering of the sensed signals 502 rather than the raw signal provided as the output from the accelerometer providing the sensed signal 502. In examples where no filtering is utilized, the rectified signal 520 may be generated, as described herein, based on the raw signal provided as the output from the accelerator providing the sensed waveform 502. In various examples, the signal 502 is generated by taking samples of the raw signal being output from a single axis of an accelerometer at some predetermined sampling rate.

As shown in FIG. 10A, a first window 504 is configured to include a width 506 enclosing a portion of sensed waveform 502. The portion of sensed waveform 502 included within first window 504 comprises the portion waveform 502 extending from a beginning time 508 to an ending time 510. The width 506 included within first window 504 is a configurable width. In some examples, width 506 of first window 504 is determined by a combination of a selected sample rate (frequency) and by a predefined number of samples of sensed waveform 502 that will be included in first window 504. By way of illustration, a sample rate for sampling the voltage level of sensed waveform 502 is set to 256 Hz, (e.g., 256 samples of waveform 502 are taken per second), and the predefined number of samples per width 506 of first window 504 is determined to be 35 samples. Using these example values, a width 506, in time, for first window 504 is approximately equal to 0.1367 seconds of sensed waveform 502, based on a time period required to take 35 samples that are taken at a rate of $\frac{1}{256}$ seconds per sample. The value of waveform 502 at ending time 510 is designated as the "current value" used to calculate a rectified value associated with the waveform 502 included within first window 504. A current value 512 corresponding to the voltage level of sensed waveform 502 is determined based on the voltage level provided as a sampled value for sensed waveform 502 at the time represented by the ending time 510. A maximum value is also determined for first window 504, the maximum value being the sample value within first window 504 that has the highest values for waveform 502. In FIG. 10A, this maximum value for first window 504 would be a value of waveform 502 taken at or near peak 512. Once the current value and the maximum value for waveform 502 within first window 504 have been determined, the current value is subtracted from the maximum value to calculate a rectified value associated with the current value defined by first window 504. For example, the value of waveform 502 taken at ending time 510 would be subtracted from the sample value of waveform 502 taken at or near peak 514, and that calculated (difference) value is used as the rectified value 524 for rectified signal 520 at the time within rectified signal 520 associated with the value of waveform 502 at ending time 510.

A corresponding set of rectified values for the rectified signal 520 are calculated for each of the sampled values from the sensed waveform 502, using a moving window that is moved over waveform 502 from left to right, representing sequential windows in time, as further described below with respect to FIG. 10B. The set of rectified values, provided over time and corresponding to the waveform 502 over that same time period, is used to form the rectified signal 520 illustrated in FIG. 10A. This rectified signal is then analyzed, as further described below, in order to detect steps taken by a patient as represented by the variations in the value of the output signal of waveform 502 and as determined based on analysis of the rectified signal 520.

Figure 10B:
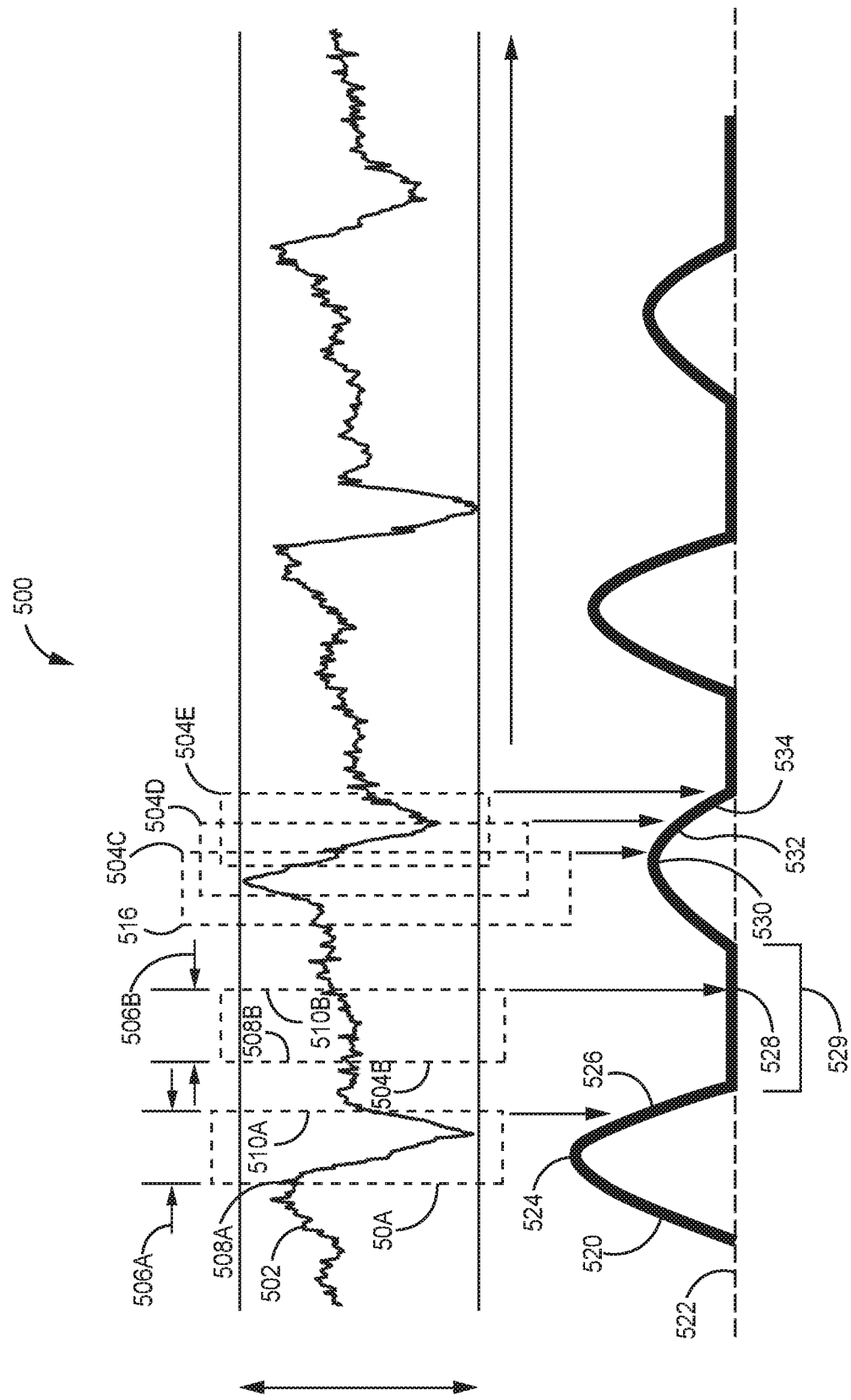
FIG. 10B is another example of graphical illustration of FIG. 10A, showing rectification of a sensed waveform in accordance with various techniques described in this disclosure.

FIG. 10B is another example of graphical illustration 500 showing rectification of the sensed waveform 502 in accordance with various techniques described in this disclosure. Sensed waveform 502 is again illustrated in FIG. 10B, with example windows 504A, 504B, 504C, 504D, and 504E imposed at various positions along waveform 502. In a manner similar to that described for first window 504 shown in FIG. 10A, each of example windows 504A, 504B, 504C, 504D, and 504E as illustrated in FIG. 10B has a width, a start time, and an ending time, and includes a portion (in time) of waveform 502 represented by a set of sample values for waveform 502 taken during a period of time enclosed within each example window, respectively.

For example, window 504A comprises a width 506A having a starting time 508A and an ending time 510A, and enclosing a number of sample values for waveform 502 over a time period of waveform 502. A "current value" for window 504A is determined by the value of the sample taken for waveform 502 at ending time 510A, and a maximum value for the samples of waveform 502 within window 504A can be determined by determining which of the sample values of waveform 502 that are enclosed within window 504A has the highest value. By subtracting the current value from the maximum value associated with window 504A, a rectified value 526 can be calculated, and plotted as a value of rectified signal 520 at a time for rectified signal 520 corresponding to the ending time 510, and thus corresponding to the current value associated with window 504A.

By way of illustration, the difference in the current value of waveform 502 and the maximum value of waveform 502 associate with window 504A is less than the difference for these corresponding sampled values associated with first window 504 as illustrated in FIG. 10A, thus resulting in a rectified value 526 that is lower (closer to baseline 522) than the rectified value 524 associated with first window 504. The lower value for rectified value 526 results in the downward direction of the curve of rectified signal 520 between the points represented by rectified value 524 and rectified value 526. In various examples, additional windows, and additional rectified samples may be generated between the rectified values 524 and 526, wherein the spacing illustrated between the portions of waveform 502 enclosed in first window 504 and example window 504A are not necessarily to proper scale, and example window 504A in some examples is not the next consecutive window configured to generate a rectified value from waveform 502 following generation of a rectified value from first window 504 used to generate rectified value 524. The spacing of the moving window, and the frequency of consecutive windows imposed along waveform 502 is not limited to a particular spacing or frequency, and is further described below with respect to examples windows 504C, 504D, and 504E.

In another example, window 504B comprises a width 506B having a starting time 508B and an ending time 510B, and includes a number of sample values for waveform 502 taken over a time period of waveform 502. A "current value" for window 504B is determined by the value of the sample taken for waveform 502 at ending time 510B, and a maximum value for the samples of window 504B can be determined by determining which of the sample values of waveform 502 that are enclosed within window 504B has the highest value. By subtracting the current value from the maximum value associated with window 504B, a rectified value 528 can be calculated, and plotted as a value of rectified signal 520 at the time for rectified signal 520 corresponding to the ending time 510B, and thus corresponding to the current value of waveform 502 associated with window 504B.

By way of illustration, the current value of waveform 502 for window 504B at ending time 510B is also the maximum value of the samples of waveform 502 that are enclosed within window 504B. Subtracting the current value for window 504B from the maximum (same) value of the samples included in window 504B results in a calculated value of zero for rectified value 528. This calculated zero value for rectified value 528 is shown as a point along the flat area 529 of rectified signal 520 that follows along at or near baseline 522.

Thus, as illustrated by example window 504A, when a maximum value within a window is greater than the current value for that window, a positive value for the rectified value associated with that window is generated, and as illustrated by example window 504B, when the current value associated with a window is also the maximum value for the samples included within the window, a value of zero for the rectified value associated with that window is generated. No negative values will result from calculating these rectified values by using the technique as described above. As such, the rectified signal 520 is considered to be a positive waveform in that all rectified values used to generate the rectified signal 520 will have either a value of zero or a non-zero positive value. In addition, by generating the rectified signal 520 in this matter, the peaks provide by rectified signal 520 will be accentuated with respect to the differences in the signal values provided by waveform 502, and thus make steps taken by a patient as represented by the waveform 502 more easily detectable using the step detection techniques further described herein and the equivalents thereof.

In various examples, each sample value included in waveform 502 is associated with a separate window of the set of moving windows, and each window generates a separate calculated rectified value associated with that window. The rectified values are arranged in a sequence in time that corresponds to the sequence of current values for the windows imposed on waveform 502 and used to calculate these rectified values, thus generating the set of rectified values comprising the rectified signal 520. As such, rectified signal 520 comprises a set of rectified values arranged in sequence over time, having a one-to-one correspondence with the set of sample values arranged in sequence over time that are represented by waveform 502. Each moving window used in the generation of the set of rectified values includes a current value represented by the last sample taken from waveform 502 at the ending time for that window, and a number of samples, for example 35 samples, taken prior to taking the last sample. In various examples, the window having this last sample and the previous number of samples is used to calculate a rectified value associated with the window, and to provide the rectified value associated with the time of the last sample for generation of the rectified signal. As a next sequential sample of waveform 502 following the last sample is received, the window is moved over so that the next sequential sample, along with the same number of previous samples (for example 35 previous samples) is now included in the moved window. In this example, the moved window would enclose the next sequential sample, the last sample from the previous window, and all of the samples included in the previous window except the oldest (in time) sample from the previous window. The samples enclosed in the moved window would then be used to calculate another rectified value to be include in rectified signal 520 and corresponding in time to the next sequential sample of waveform 502.

This pattern of receiving a next sample of waveform 502, moving the window over to include the next sample, and calculating additional rectified value corresponding to each move of the window is repeated at some defined rate or frequency to generate the set of rectified values used to provide rectified signal 520. An example illustration of movement of the window along waveform 502 over time is shown in FIG. 10B as windows 504C, 504D, and 504E. Window 504C has a start time at point 516, and encloses a number of sample values of waveform 502. Based on these enclosed samples, a rectified value 530 is calculated and provided as a point along rectified signal 520. Window 504D is a window having a same width as window 504C, but moved to the right (later in time) along waveform 502 to enclose a sample of waveform 502 generated later in time than the latest sample (in time) included in window 504C. Window 504D overlaps with window 504C, and thus includes many of the same sample values enclosed by window 504C, plus at least one or more new sample values. Once the moving window is positioned as shown for window 504D, the current value and the maximum value for window 504D can be determined, and a rectified value 532 associated with window 504D is calculate and provided as described above with respect the rectified value 530.

Repeating this procedure, window 504E is a window having a same width as window 504C and 504C, but moved to the right (later in time) relative along waveform 502 to enclose a sample of waveform 502 generated later in time than the latest sample (in time) included in window 504D. In some examples, window 504E overlaps with window 504C and 504D, and thus includes many of the same sample values enclosed by window 504C and 504D, plus at least one or more new sample values. Once the moving window is positioned as shown for window 504E, the current value and the maximum value for window 504D can be determined, and a rectified value 532 associated with window 504D is calculate and provided as described above with respect the rectified value 530.

By repeating the same pattern of moving the window to the right (later in time) over waveform 502 and generating a rectified value for each window (such as rectified values 530, 532, 534) based on the sample values enclosed in each window, respectively, the rectified signal 520 can be generated. In various examples, a rectified value is generated for each sample value provided in waveform 502, and therefore the spacing of windows imposed over waveform 502 is based on the sample rate used to generate waveform 502. However, in other examples a window is imposed over waveform 502 and moved to a new location along waveform 502 based on a predetermined time interval, and not necessary tied to the timing (spacing) of the sample rate used to generate waveform 502. In various examples, generation of the rectified signal 520 comprises using one or more curve fitting techniques, as would be understood by one of ordinary skill in the art, to generate a continuous curve for rectified signal 520 based on the sequence of rectified values generated by the processing of the moving windows and the sample values provided by waveform 502 as described above. Once a rectified signal, such as rectified signal 520, has been generated in whole or in part, analysis of the rectified signal can be performed to detect steps taking by a patient as represented by the variations in the waveform 502. Further illustration and description of the step detection process is provided for example with respect to FIG. 11 and FIG. 12.

Figure 11:
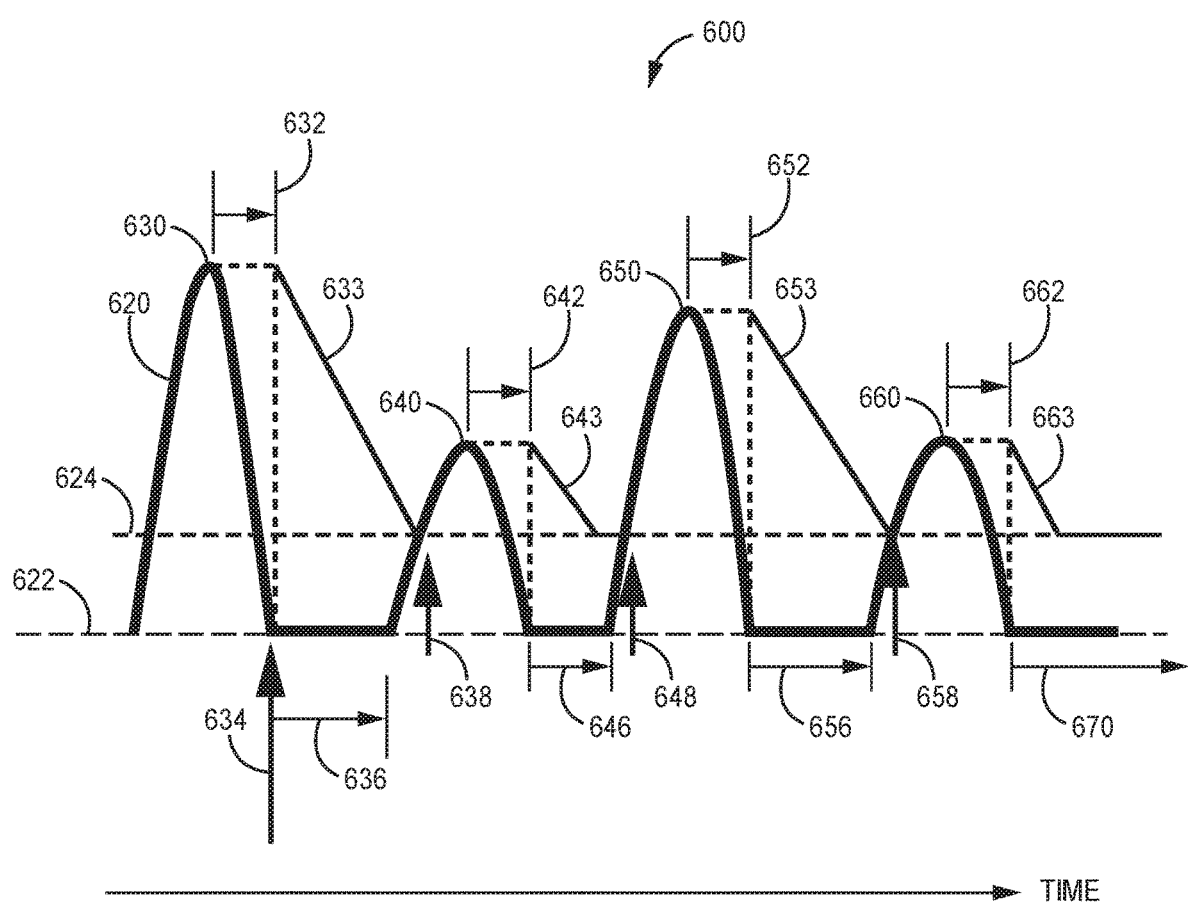
FIG. 11 is another example graphical illustration of another example rectified signal in accordance with various techniques described in this disclosure.

FIG. 11 is a graphical illustration 600 of an example rectified signal in accordance with various techniques described in this disclosure. Graphical illustration 600 includes a rectified signal 620 having a baseline value illustrated by dashed line 622, and a threshold floor value represented by dashed line 624. Rectified signal 620 comprises a curve representative of a set of calculated rectified values corresponding to a sensed waveform generated by a single axis accelerometer in response to measured acceleration forces generated by a patient taking steps, for example while either walking or running. In various examples, rectified signal 620 is rectified signal 520 illustrated and described with respect to FIGS. 10A and 10B.

As illustrated in FIG. 11, rectified signal 620 includes variations in the calculated rectified values corresponding to the sensed waveform generated by a single axis accelerometer, as described above, over a period of time, the values moving sequentially in time as the graph moves from the left-hand side toward the right-hand side in FIG. 11. In various examples, the vertical variations in the rectified signal 620 represent variations in gravitational units present in the rectified signal, wherein each unit along the vertical scale of rectified signal 620 is 0.0125 g units of gravitational force, using gravity having a force of 9.80991 m/s². Initially, the rectified value of signal 620, begins at or near the baseline value 622, which represents a value of zero. The value of signal 620 begins to increase, rising above a value associated with the threshold floor 624, and rises to a maximum value at peak 630 before beginning to decrease in value back toward the baseline value 622. A time period 632 passes between the time signal 620 reaches the peak value 630 and the time signal 620 returns to the baseline value 622, the time when signal 620 returns to baseline value 622 indicated by arrow 634. Once the values of signal 620 has returned to the baseline value 622, an auto-adjusting threshold value, represented by threshold line 633, is initiated to a value equal to the value of signal 620 at the peak 630, and begins to decrease in value from the initialized value. In some examples, instead of initiating the decrease in the auto-adjusting threshold value when signal 620 returns to a value of the baseline value (e.g., a value of zero), the initial value of the threshold is decreased beginning at a time when the value of signal 620 first decreases to some predetermined value above the baseline value, such as a value of 7 units (e.g., 7 units times 0.0125 g/unit=0.0875 g of gravitational force). The rate (slope) of the decrease in the value of the auto-adjusting threshold line 633 may be determined, at least in part, by the maximum value associated with peak 630. For example, a rate of decrease (downward slope) for the auto-adjusting threshold may be set as a ratio or a multiple of the peak value 630. In some examples, the slope for the auto-adjusting threshold is set to a value of 1.8 times the value at the peak 630 for signal 620. Once the auto-adjusting threshold value is set, and the rate of decrease for the threshold value is determined, and the value of rectified signal 620 has returned to the baseline value 622 at the time indicated by arrow 634, the value of the auto-adjusting threshold begins to decrease from the initial value, at a rate indicated by threshold line 633, until the auto-adjusting threshold value returns to a value equal to the threshold floor 624, our until the auto-adjust threshold value again is equal to the current value of signal 620.

As shown in FIG. 11, the auto-adjusting threshold value begins to decrease starting at the time represented by arrow 634, corresponding to the same time when signal 620 returns to baseline value 622 from peak 630. During the time period represented by arrow 636, signal 620 remains at or near a value equal to the baseline value 622, and below the value of the threshold floor 624. During this time period, the value of the auto-adjusting threshold value continues to decease at a rate defined by threshold line 633. At the end of time period represented by arrow 636, the value of signal 620 begins to increase, and at a time represented by arrow 638, has risen to a value at least equal to the value set by the threshold floor 624, and the auto-adjusting threshold value is now equal to the value of the signal 620. When this occurs, a step is considered to be detected at the time represented by arrow 638.

Following the detection of a step at time 638, the value of signal 620 continues to increase to a peak value 640, and then begins to decrease. In some examples, once signal 620 reaches peak value 640 and begins to decrease, the value of the auto-adjusting threshold is reset to an initial value equal to the value of signal 620 at peak 640. In other examples, the initial threshold value may start at some value other than the peak value, for example at a percentage of the peak values, or the peak value plus or minus the predetermined value. A time period 642 passes between the time signal 620 reached the peak 640 and the when signal 620 returns to the baseline value 622, the time when signal 620 returns to baseline value 622 indicated by the beginning of the time period represented by arrow 646. Once the value of signal 620 has returned to the baseline value 622 after having risen to peak 640, an auto-adjusting threshold value, represented by threshold line 643, is initiated to a value equal to the value of signal 620 at the peak 640, and begins to decrease in value from the initialized value. The rate (slope) of the decrease in the value of the auto-adjusting threshold line 643 may be determined, at least in part, by the maximum value associated with peak 640. For example, a rate of decrease (downward slope) for the auto-adjusting threshold may be set as a ratio or a multiple of the peak values 640. In some examples, the slope for the auto-adjusting threshold is set to a value of 1.8 times the value at the peak 640 for signal 620. Once the auto-adjusting threshold value is set and the rate of decrease for the threshold value is determined, and the value of rectified signal 620 has returned to the baseline value 622, the value of the auto-adjusting threshold begins to decrease from the initial value, at a rate determine by threshold line 643, until the auto-adjusting threshold value returns to a value equal to the threshold floor 624, or until the auto-adjust threshold value again is equal to the current value of signal 620. In various examples, because the rate of decrease (slope) for sloped line 643 is determined by the amplitude value of peak 640, and because the amplitude value of peak 640 may be different from the amplitude value of signal 620 at peak 630, the rate of decrease (downward slope) of the auto-adjusting threshold following peak 640 may be different, in some examples flatter (e.g., a slower rate of decrease) than was utilized for the rate of decease for the auto-adjusting threshold during the time period following peak 630 and prior to peak 640. This is referred to as an 'adaptive slope" process because the slope of the threshold line, and thus the rate of decrease of the initialized threshold value following a peak in the rectified signal, is determined based on the amplitude of the previous peak.

During the time period represented by arrow 646, signal 620 remains at or near a value equal to the baseline value 622, and below the value of the threshold floor 624. During this time period, the value of the auto-adjusting threshold continues to decease at a rate defined by sloped line 643. The auto-adjusting threshold continues to decrease until the auto-adjusting threshold value returns to a value equal to the threshold floor 624, or until the auto-adjust threshold value again is equal to the current value of signal 620. As illustrated in FIG. 11, the auto-adjusting threshold decreases to a value equal to the threshold floor 624 before the value of signal 620 again rises to a value of the threshold floor 624. In these instances when the value of the auto-adjusting threshold reaches the threshold floor 624, the value of the auto-adjusting threshold stops decreasing in value and remains at the value established by the threshold floor 624. At the end of time period represented by arrow 646, the value of signal 620 begins to increase, and at a time represented by arrow 648, has risen to a value equal to the value set by the threshold floor 624. When this occurs, a step is considered to be detected at the time represented by arrow 648.

The above described pattern is repeated to determine detection of a step for each addition rise of signal 620 to a peak value above the threshold floor value, returning to a value at or near the baseline, and then rising again to a value of at least the threshold floor. For example, as illustrated in FIG. 11, following the time indicated by arrow 648, signal 620 rises to a value incited by peak 650, and then deceases back to a value at or near the baseline value 622. Once peak 650 has been detected, the auto-adjusting threshold is initialized to a value based on the value of the rectified signal 620 at peak 650, and a rate of decrease (downward slope) for the initial value of the auto-adjusting threshold is determined as sloped line 653. Once signal 620 returns to the baseline value 622, the auto-adjusting threshold begins decreasing at a rate determined by threshold line 653, and continued to decease unit the value either equals the value set by the threshold floor 624, or again equal the value of rectified signal 620. During the time period indicated by arrow 656, the value of rectified signal 620 returns to the baseline value 622, and remain at or near the baseline value 622 during the time period indicated by arrow 656. Following the time period indicated by arrow 656, the value of rectified signal 620 begins to rise, and at the time indicated by arrow 658 rises to a value equal to the threshold floor 624, and to a value hat is equal to the threshold values. Based on these occurrences, another step is considered to have been detected at the time represented by arrow 658.

Following the time indicate by arrow 658, rectified signal 620 again rises to a peak value illustrated as peak 660, and decreased back to at or near the baseline value 622 at the time indicated by arrow 670. An initial value and a rate of decrease, the rate of decree indicated by threshold line 663, are determined for the auto-adjusting threshold value as describe above. The auto-adjusting threshold value begins to decrease once the rectified signal 620 returns to the baseline value 622. If the rectified signal 620 again rises to a value above the threshold floor 624 and to a value equal to the threshold value, a determination is made of the detection of another step (not shown in FIG. 11).

In various examples, at time interval comprising the time interval that elapses between a current detected step and a prior detected step is measured, and is compared to determine if the measured elapsed time falls within a predetermined upper and lower range of time limits. For example, a lower predetermined time limit may be set at 0.33 seconds, representative of the time between steps when a patient is walking or running at a rate of 180 steps per minute. In this same example, an upper predetermined time limit may be set at 2.0 seconds, corresponding to a time between steps when a patient is walking or running at a rate of 30 steps per minute. It would be understood by one of skill in the art that these step rates, and thus the corresponding upper and lower predetermined time limits, are examples, and different predetermined time limits for the upper time limit, for the lower time limit, or for both the upper time limit and the lower time limit may be configured for use in the methods and by the devices configured to detect step as disclose herein and the equivalents the thereof. In various examples, the lower predetermined time limit is based at least in part on the amplitude of the rectified signal in the peak detected just prior to detection of a potential step, and is adjusted automatically during each step. In some examples, if the rectified signal peak has a value greater than 10 units (e.g., 10 units times 0.0125 g/unit=0.125 g of gravitational force) but less than a value of 56 units (e.g., 56 units times 0.0125 g/unit=0.7 g of gravitational force), the predetermined lower limit for the elapsed time range for the next potential step is set to a value of 3.3 Hz (approximately 0.303 seconds) and if the next step occurs within an elapsed time period of less than 0.303 seconds, the step is rejected. In some examples, if the rectified signal has a peak value of greater than 56 units, reject any subsequent step that has a rate in excess of 3.6 Hz (e.g. lower time limit set approximately 0.278 seconds) relative to the prior step. In various examples, if the rectified signal has a peak value less than 10 units, reject the next subsequent step that is faster than 2.0 Hz (e.g., set the lower time limit at approximately 0.5 seconds). In various examples, any step whose elapsed time relative to the previous step is slower than 0.1 Hz (10 seconds) is rejected.

Using the example values of 0.033 seconds as a lower time limit and 2.0 seconds as an upper time limit, the elapsed time for each current step relative to the step detected prior to the current step is measured. If the measured elapsed time associated with the prior step and the current step falls within the range or 0.33 to 2.0 seconds, or in some examples is equal to one of these values, then the current step is considered a "qualified" or a "qualifying" step, and in some examples, is counted. Counting refers to in some examples incrementing a value stored in a counter that is tracking a total number of detected and/or qualifying detected steps. In some examples, a predetermined number of consecutive steps must be counted before subsequent steps will be used to increment a counter value used for recording the number of detected steps. For example, a predetermined number of consecutive steps that must be counted before subsequent steps are used to increment a counter is set to a value of three. Using these examples, before any detected steps will be allowed to increment a value of a counter used to record the number of detected steps, three consecutive steps must be detected, each steps having an elapsed time between that step and the previous step that falls within, or in some examples is equal to one of the upper and the lower predetermined time limits (e.g. 0.33 to 2.0 seconds). If three consecutive steps are detected that each meet the time limit criteria passed on the predetermined upper and lower time limits, any subsequent step that is detected, and that also meets the time limit criterial, will cause a counter used to record the number of detected steps to be incremented. In various example, incrementing the counter comprises incrementing the counter value by a value of one for each subsequently detected step once the predetermined minimum number of qualify steps has been detected, and as long as the subsequent step is also a qualifying step. In various examples, when counting subsequently detected steps, if a subsequently detected step is not a qualifying step, for example the elapsed time between the subsequent detected step and the previously detected step is too long or too short a time, the subsequent step does not cause the counter to be incremented. In addition, if a non-qualifying subsequent step is received, incrementing the counter based on detected step will not again be initiated until the predetermined number of consecutive and quality steps has again been detected.

Figure 12:
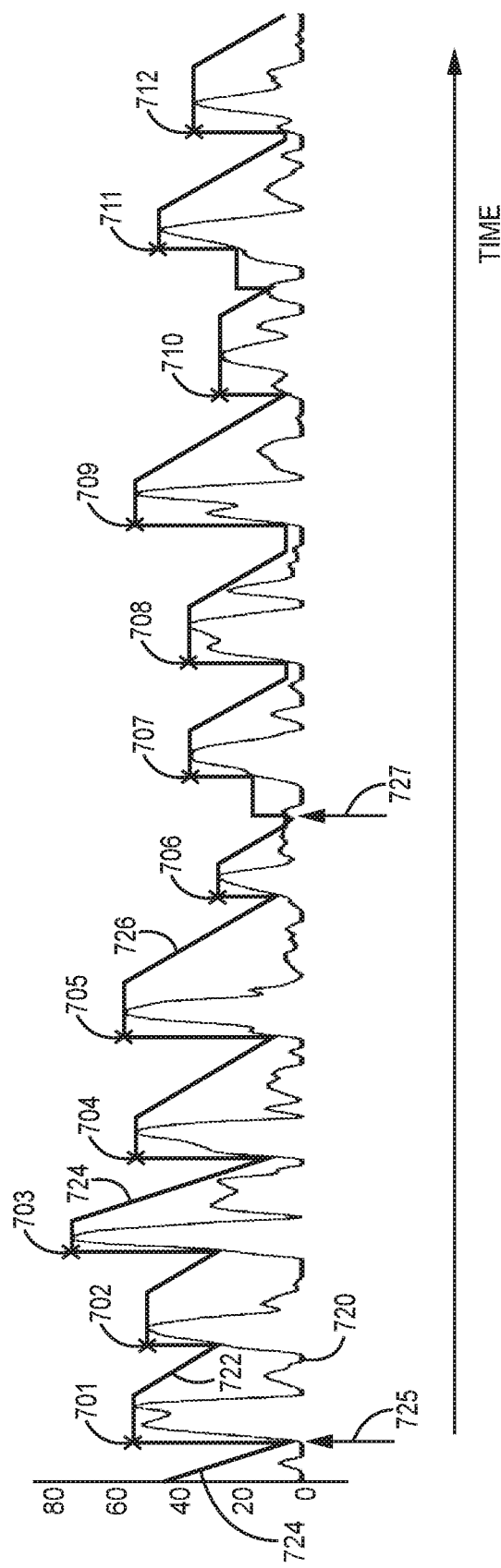
FIG. 12 is another example graphical illustration of another rectified signal according to various techniques described in this disclosure.

FIG. 12 is a graphical illustration 700 of a rectified signal 720 according to various techniques. Graphical illustration 700 illustrates a rectified signal 720 and an associated auto-adjusting threshold line 722. Rectified signal 720 may be a signal generated from a sensed waveform provided as an output from a single axis accelerometer coupled to a patient as described herein, using the rectification techniques described herein or the equivalents thereof. As shown, rectified signal 720 includes multiple variations of a signal value relative to a baseline (zero) value over a period of time. The threshold line 722 as illustrated in FIG. 12, is representative of a threshold value corresponding to the value of the rectified signal 720 over time. As shown in FIG. 7, a series of "X" marks, indicated as reference numbers 701 through 712, are located along the threshold line 722, and indicate the detection of twelve steps, respectively, over the time period represented by rectified signal 720. For example, an initially decreasing value for the threshold line, represented by sloped line 724, corresponds to the value of rectified signal 720 at time 725. Because sloped line 724 has been set up following a detected peak of rectified signal 720 (peak not shown in FIG. 7), and intersects the rectified signal 720 while signal 720 is rising and following a period of time when rectified signal 720 returned to a value at or near the baseline (zero) value, the intersection is determined to a detected step, specifically step 701.

Following the detection of step 701, rectified signal 720 continues to rise in value until a new peak is detected, after which rectified signal 720 decreases back to having a value at or near the baseline value. As a result of the peak following detected step 701, a threshold value and a rate of decrease for the new threshold value is determined. The new rate of decrease for the threshold line 722 is illustrated by sloped line 722. As the threshold line 722 begins to decrease in value, rectified signal 720 begins to increase in value from the baseline value. When the value of the threshold line 722 again equals the value of the rectified signal 720, a next step 702 is determined to have been detected. The pattern of resetting the threshold line value and rate of decrease of the threshold line value following a peak in the rectified signal 720, and decreasing the threshold line value until the threshold line value equals the value of the rectified signal 720 after the rectified signal 720 returns to the baseline and then begins to rise from the baseline value is repeated, and results in the detection of successive steps 703 through 712 following the detection of step 702.

As shown in FIG. 12 the amplitude of the various peaks following the detection of a step are not of equal amplitude. For example, the amplitude of the next peak of rectified signal 720 following the detection of step 703 is higher in amplitude than for example the amplitude of the next peak of signal 720 following the detection of step 705. As a result, the slope of the decrease in the value of the threshold line 722 following the detection of step 703, as represented by sloped line 724, is steeper (more downward sloping) than the slope of sloped line 726, representing the rate of decrease for threshold line 722 following the detection of step 705. In changing the slope of the threshold line 722 following a step detection and the next subsequent peak in rectified signal 720, the threshold line 722 is "auto-adjusting" based on the variations in the rectified signal 720.

In some examples, the pattern described above with respect to the rectification signal 720 and the threshold line 722 occurs, but a determination is made that the pattern does not represent a qualifying step. By way of illustration, at the point in time indicated by arrow 727 in FIG. 12, the value of threshold line 722 is equal to the value of rectified signal 720, following a peak and a return to the baseline value for rectified signal 720. However, this pattern is not detected as a step because in some examples the time period between the detection of step 706 and the time indicated by arrow 727 is too short, in other words does not meet the lower time limit for a minimum elapsed time between a step and the previously detected step. In various examples, the occurrence illustrated at arrow 727 will not be counted as a qualifying step, and is not used to increment a value of a counter being used to track and count detected and qualifying steps.

Figure 13:
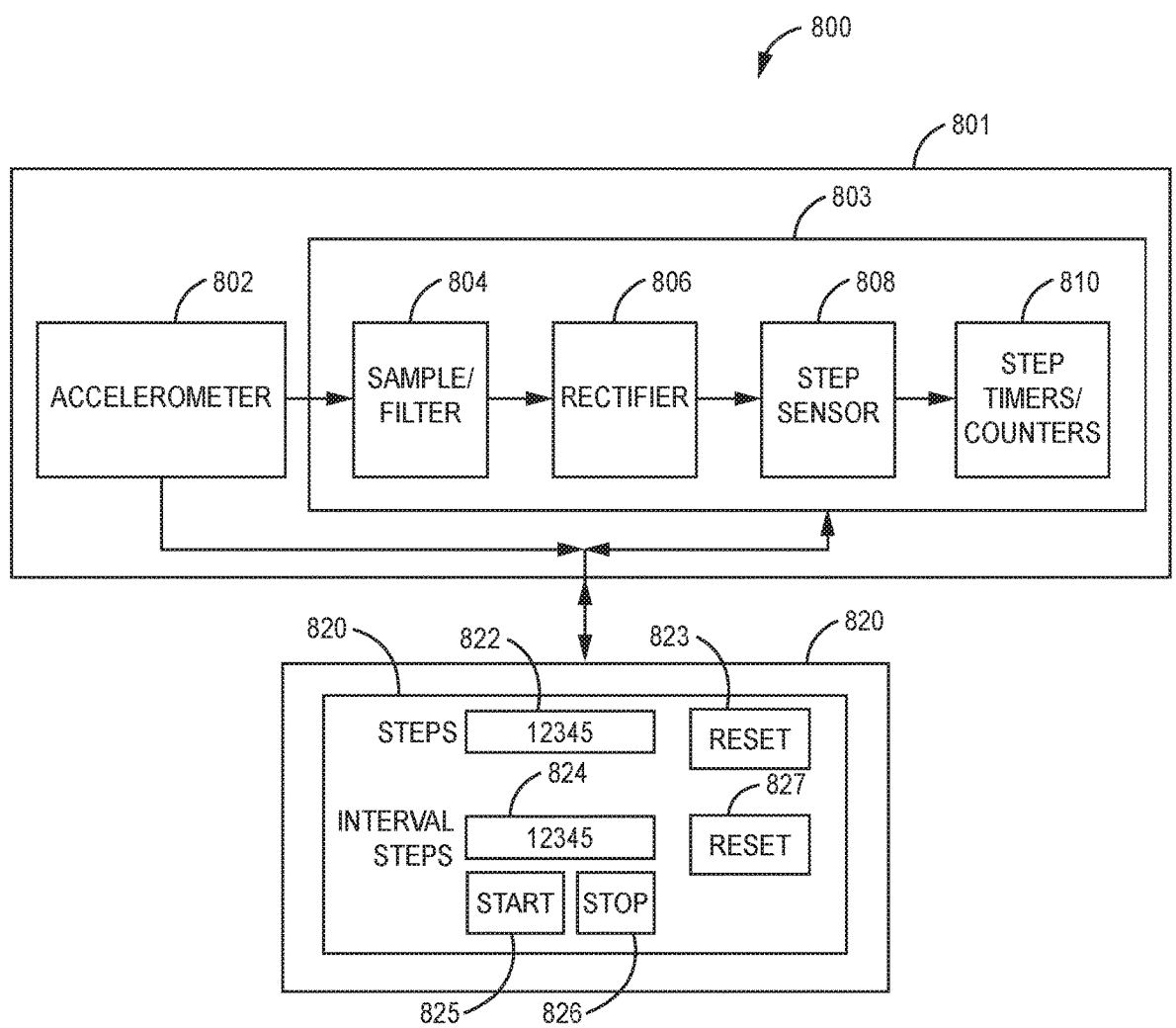
FIG. 13 is a block diagram illustrating a system in accordance with various techniques described in this disclosure.

FIG. 13 is a block diagram illustrating a system 800 in accordance with various techniques described in this disclosure. System 800 includes circuitry 801 that may be included in an implantable medical device, such as any of ICD 10A, ICM 10B, ICD 10C, IPD 10D, or another IMD configured to implement the techniques of signal processing, signal rectification, and step detection as described herein. Circuitry 801 includes an accelerometer 802 coupled to processing circuitry 803. In various examples, accelerometer 802 and processing circuitry 803 correspond to an accelerometer and processing circuitry physically located within these implantable devices. In the alternative, processing circuitry 803, in part or in whole, may correspond to other proceeding circuitry that is located outside of the implantable device, for examples in any of the one or more external devices described herein. In various examples, accelerometer 802 configured to provide an output signal to processing circuity 803. In various examples, the output signal provided by accelerometer 802 is a waveform, such as waveform 502 illustrated and described with respect to FIGS. 10A and 10B, representing of a variation in acceleration values that may include variations generated when a patient coupled to circuitry 801 takes steps, such as when walking or running. Circuitry 801 may be coupled to external device 820. In various examples, external device is any of external device 30A as shown and described with respect to FIG. 1, external device 30B as shown and described with respect to FIG. 3, external device 30C as shown and described with respect to FIG. 4A, or external device 30D as shown and described with respect to FIG. 5.

In various examples, circuity 801 includes processing circuitry 803 that includes a sample/filter circuit 804, a rectifier circuit 806, a step sensor circuit 808, and one or more step timers/counters 810. In various examples, sample/filter circuit 804 filters the output signal provided by the accelerometer 802 to provide a filtered output signal. In some examples, sample/filter circuit 804 is configured to receive the output signal generated by accelerometer 802, or the filtered signal generated from the output signal, and to sample the output or the filtered signal at some sample rate to provide a waveform representative of the variations value of the output signal over time.

The output signal from the sample/filter circuit 804 is provided to rectifier circuit 806. Rectifier circuit 806 is configured to "rectify" the output signal using any of the techniques described herein, or the equivalents thereof, to generate a rectified signal. In various examples, the rectified signal generated by rectifier circuit 806 is any of rectified signal 520 as illustrated and described with respect to FIG. 10A-B, rectified signal 620 as illustrated and as described with respect to FIG. 11, or rectified signal 720 as illustrated and described with respect to FIG. 12. Rectifier circuit 806, having received the output signal from sample/filter circuit 804, is configured generate a rectified signal from the received signal, and to provide the rectified signal to step sensor circuit 808. Step sensor circuit 808 is configured to receive the rectified signal from rectifier circuit 806, and to performs analysis of the rectified signal to determine when/if steps are present as represented by the variation provided in the rectified signal. Step sensor circuit 808 may be configured to perform detection of steps represented by the rectified signal using any of the step detection techniques described herein, and the equivalents thereof.

When step sensor circuit 808 detects a step, step senor circuit 808 may be configured to output a signal representative of the detection of a step to step timers/counters 810. In various examples, the output signal can be a voltage pulse having some predetermined amplitude and/or duration. However, the output signal provided by step senor circuit 808 is not limited to a voltage pulse, and may comprise any type of signal that can be received by timers/counters 810 and interpreted as an indication of the detection of a step. The output signal indicative of the detection of a step as provided by step sensor circuit 808 is provided as an input to timers/counters 810. In various examples, each time an indication that a step has been detected is received at timers/counters 810, a counter value of a counter within timers/counters 810 is incremented. The incremented counter value is stored until another such indication of a detected step is received by circuit 810, or until circuit 810 receives a signal indicating that the counter value is to be reset, for example to a value of zero. In various examples, circuit 810 includes at least one timer, the timer configured to determine an elapsed time that has occurred between receiving an indication of the detection of a step and receipt of the indication of detection of the previous step. For example, when an indication of the detection of a step is received at timers/counters 810, the timer is initiated and begins to track the time that elapses until a next indication of a detected step is received at counter 810. The elapsed time is then compared to upper and lower time limits to see if the elapsed time falls within time range defined by the upper and lower time limits. If the elapsed time does fall within the time range defined by the upper and lower time limits, the step associated with the last received indication of a detected step is considered to be a qualifying step, and the counter tracking the number of qualifying steps is incremented by a value of one. If the elapsed time does not fall within the time range defined by the upper and the lower time limits, the step is not considered to be a qualifying step, and the counter tracking qualified steps within counter 810 is not incremented as a result of receiving the indication of this latest detected step. Thus, in various examples only qualifying steps are used to increment a counter value as a result of timers/counters 810 receiving an indication of detection of a step from the step sensor circuit 808.

In various examples, timers/counters 810 includes more than one counter, wherein a first counter may be configured to count detected and/or qualifying steps until the counter is reset, and wherein one or more other counters may be configured to start and stop counting detected and/or qualifying steps based on input signals received by timers/counters 810. For example, one or more of the counters included in timers/counters 810 may be configured as an interval counter, and to ignore indications that a step has been detected until a "start" signal for that counter is received by timers/counters 810. Following receipt of the start signal, the interval counter will begin to count each of the received indications of a detected and/or qualifying steps until another signal, indicative of a "stop" signal, is received by timers/counters 810. In various examples, the value stored in the interval counter will be maintained in the interval counter until a "reset" signal is received by timers/counters 810.

The interval counter in addition to a base counter is useful for additional tracking of steps over a predetermined session, such as a therapy session, or over a predetermined event, such as when a patient coupled to circuity 801 goes for a walk. By having a separate interval counter tracking of steps over a session or event may be counted without the need to reset or otherwise affect a counter value being tracked by a base counter, wherein the base counter can track detected and/or qualified steps over a different time period, such as a day, a week, or a year as compared to the time interval over which to the interval counter is counting detected and/or qualify steps.

As illustrated in FIG. 13, circuitry 801 is communicatively coupled to an external device 820. External device 803 is not limited to any particular type of deice, and may be any of the external devices described herein, including external programmers as described herein. In various examples, external device 820 is a mobile device, such as a cellular phone or a laptop computer. As shown in FIG. 13, external device 820 includes a display 821 configured to provide a visual display of information. Display 821 is not limited to any particular type of display, and may be any type of visual display, such as display screen of a cellular phone or a laptop computer, or for example a computer monitor. In various examples, external device comprises one or more display fields 822, 824, configured to display an indication of one or more counter stored in any of the counters included in timers/counters 810. By way of example, display field 822 is configured to display an indication, such as a number value, indicative of the value stored in a base counter of timers/counters 819. In various examples, display 821 comprises a reset button 823 that when actuated, provides a signal from external device 820 to timers/counters 810 causing the counter value stored in the base counter to be reset, for example to a value of zero. In another example, display field 824 is configured to display an indication, such as a number value, indicative of the value stored in an interval counter of timers/counters 819. In various examples, display 821 comprises a start button 825, a stop button 826, and a reset button 827. As described above, the interval counter can be used to count detected and/or qualifying step over a predefined time period or during a particular event. To initial the interval counter, the start button 825 is actuated, and external device then sends a signal to timers/counters 810 to activate the interval counter. Once actuated, the interval counter will be incremented each time an indication of a detected and/or qualify step is received by timers/counters 810. The value currently stored in the interval counter will be displayed in display field 824. The interval counter will continue to be incremented base on receipt of the detected and/or qualifying step signal until the stop button 826 is pressed, at which time external device 820 will send a signal to the timers/counters 810 to stop incrementing the interval counter. When stopped using the stop signal, interval counter will maintain the counter value present at the time the stop signal was received, wherein that counter value may also be displayed in display field 824. When the reset button 827 is actuated, external device 820 is configured to send a reset signal to timers/counter 810 that will cause the value stored in the interval counter to be reset, for example to a value of zero.

In various examples, one or more of the above functions described as being performed by processing circuitry 803 may instead be performed by external device 820. For example, the output signal from accelerometer 802 may be provided directly to external device 820, and the functions described above as being performed by processing circuity 801 are provided instead by similar processing circuitry (not shown in FIG. 13) located in external device 820. In various examples, some portion or portions of the processing functions described above as being performed by processing circuitry 803 may instead be performed by processing circuity (not shown in FIG. 13) located in external device 820.

Figure 14:
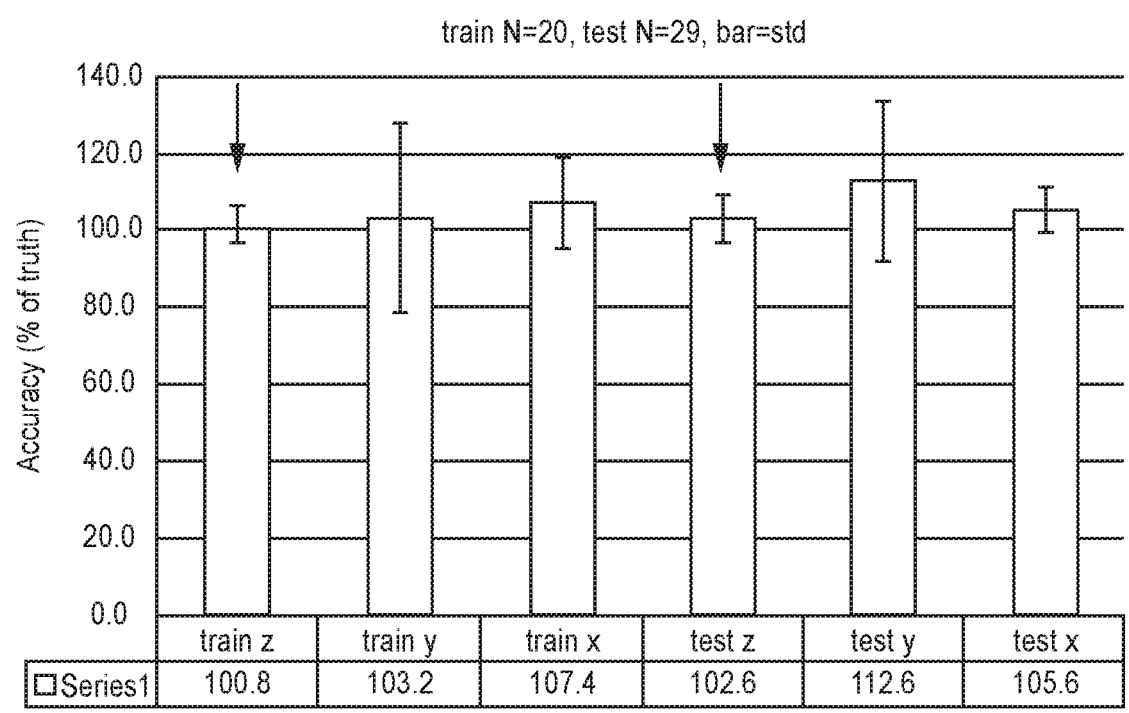
FIG. 14 is a graphical illustration of the test results of three sets of training parameters X, Y and Z, and the actual test results achieved when operating any devices according to the techniques described herein.

FIG. 14 is a graphical illustration 850 of the test results of three sets of training parameters X, Y and Z, and the actual test results achieved when operating any device according to the techniques described herein, using test parameters X, Y, and Z during separate test sessions.

Figure 15:
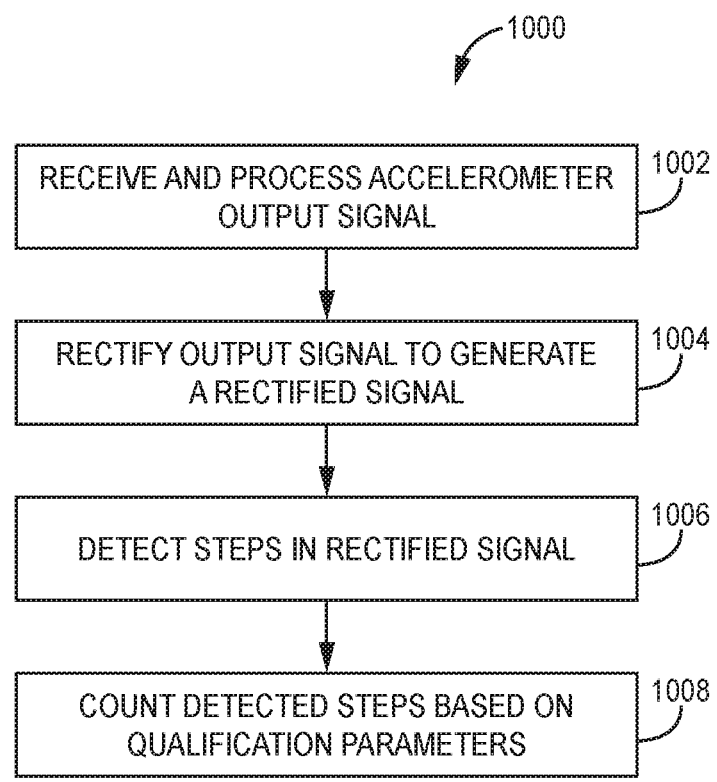
FIG. 15 is a flow diagram illustrating an example method 1000 that may be implemented by a medical device system to detect and to track steps taken by a patient coupled to system.

FIG. 15 is a flow diagram illustrating an example method 1000 that may be implemented by a medical device system to detect and to track steps taken by a patient coupled to system. For ease of description, the example method 100 is described as being performed by processing circuity 160 of IMD 10. However, example method 1000 is not limited to being performed by IMD 10, and may be implemented by any of the devices described herein, or other medical device systems configured to provide the features of example method 1000.

According to example method 1000, IMD 10 receives and processes an accelerometer output signal (block 1002). In various examples, the accelerometer output signal is a single axis accelerometer output signal. In various examples, the single axis accelerometer output signal is provided by an accelerometer oriented to detect variations in acceleration forces along a sagittal axis relative to a patient that is coupled to the accelerometer. In various examples, processing the output signal comprises filtering the output signal using a low pass filter. In various examples, processing the output signal comprises sampling the value of the output signal to determine the value of the output signal at various times base on a sampling rate.

ICM 10 rectifies rectify the output signal to generate a rectified signal (block 1004). In various examples, rectification of the output signal comprises rectification of an output signal that has been filtered by a low pass filter. In various examples, rectification of the output signal comprises imposing a set of moving windows over the output signal, and for each of the moving windows, calculating a rectified value based on a current value and a maximum value enclosed within the window. In various examples, calculating the rectified value for a window comprises subtracting the current value from the maximum value of the output signal enclosed within the window.

ICM 10 analyzes the rectified signal to detect steps represented by the variation of the rectified signal (block 1006). In various examples, analysis of the rectified signal to detect steps includes detecting a peak in the rectified signal, setting an initial threshold value based on an amplitude of the detected peak, determining a rate for decreasing the threshold value based on the amplitude of the detected peak, determining when the value of the rectified signal has returned to a baseline value following the detected peak, decreasing the threshold value at the determined rate until the threshold value is either equal to a threshold floor value or is equal to the value of the rectified signal, and detecting a step when the value of rectified signal rises to a value above the threshold floor value and is equal to the threshold value.

ICM 10 counts steps based on qualification parameters (block 1008). In various examples, ICM 10 determines if an elapsed time period between an indication of the detection of a step and the time when the previously detected step was detected falls within a time range defined by an upper and a lower time limit. If the elapsed time falls within the time range, the detected step is determined to be a qualifying step, and is counted. If the elapsed time does not fall within the time range, the detected step is not counted.

Various features of the devices and methods described herein include:
  "Rectify"
  Use samples from frontal axis filtered signal
  Initialize first window (n=30 samples)
  Find Maximum value in window
  Create Rectified Signal (RS) by subtracting Current value from Maximum value
  RS(i)=Maximum−Current(i)
  Shift window one sample (i+1)
  Calculate next RS(i) value
  Sense Step
  Start with adjustable Threshold set at programmed setting
  Threshold(i)=programmed setting (default is a constant, 5)
  If RS(i)>Threshold(i), then step event
  Find index of the maximum value in RS(i:i+30), set the Threshold(i:max index)=maximum amplitude
  Wait (blanking) until RS(i) reaches 7 to start a decreasing Threshold(i)
  Linear decreasing Threshold(i) from maximum amplitude during blanking to the programmed setting
  The slope will be vary based on the signal amplitude, steeper slope for higher amplitude
  Higher amplitudes occur during faster walking (i.e. walking/jogging)
  Lower amplitudes occur during slower walking (i.e. shuffling)
  If RS(i)>threshold(i), then step event
  Increment Step Counter
  Temporary Step (TS) counter=0
  Calculate time between step events. 1/step time=step rate.

Increment TS counter if step rate is slower than 3.6 Hz
when walking/jogging or is slower than 1.5 Hz when
shuffling.

Continue to increment TS counter as long as each step
interval within range

If step interval outside range
   If TS counter>=3, then Permanent Step (PS)
counter=PS+TS counter TS counter=0

End

Adjustable variables that may be set to different values according to the techniques described herein include but are not limited to the following:

Slope for rate of decrease of the threshold value—for example a steeper downward slope may be used when the peak value of the rectified signal is greater than a 1g force level.

Window size for moving window imposed on output signal—e.g., vary the number of sample values of the output signal included (enclosed) by each window The values associated with the threshold floor The threshold amplitude start value—e.g., the initial threshold value set following detection of a peak in the rectified signal The threshold start time—e.g., the time or "blanking period" allowed to elapse between the time the rectified signal reached a peak value (above the threshold floor) and the time to begin decreasing the initial threshold values set following the detected peak value in the rectified signal.

In General:

Provides a step detection device and methods comprising adaptive slope and adaptive rate rejection algorithm to perform step detection of a person or a patient based on an output signal from a single axis accelerometer Usability: To increase detection accuracy by reducing over and under sensing in step detection device.

Various aspects of the techniques described herein may be implemented in hardware, in software, in firmware, or some combination of hardware, software, and/or firmware. Variables that may be implements by any of these techniques include examples implemented in pseudocode including:

Firmware variables: (bold font is variable name in cadence_detect10)

Maximum Difference ("Rectify") Window size (e.g. 30 samples): win

Shuffling step duration minimum (e.g. 0.67 seconds=1.5 Hz): maxShufflingHz

Walking/jogging step duration minimum (e.g. 0.28 seconds=3.6 Hz): maxWalkingHz

Step duration maximum (e.g. 10.0 seconds=0.1 Hz): minShufflingHz

Number of steps required on TS counter to add to PS counter (e.g. 3)

Baseline Threshold settings (5): thr

Amplitude threshold for each slope: mvThr

Slopes for each amplitude threshold: slope, steeperMultiplier

% of maximum amplitude to begin decay (e.g. 100%)

Threshold to begin decay (current set to 7): startToDecayThr

Time delay to begin decay after RS(i) reaches Threshold (e.g. 0 seconds).

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of this disclosure have been described. These and other aspects are within the scope of the following claims.

What is claimed is:

1. A medical device system comprising:
an accelerometer circuitry configured to output a signal indicative of variations in accelerations along a single axis of movement of a patient; and
processing circuitry configured to:
receive the output signal from the accelerometer, and to rectify the output signal to generate a rectified signal, wherein rectification of the output signal comprises generating a rectified value for each of a plurality of moving windows imposed over the output signal, wherein generating the rectification value for each of the plurality of moving windows comprises determining a current value of the output signal for the window, determining a maximum value for a portion of the output signal enclosed by the window, and subtracting the current value from the maximum value; and
analyze the rectified signal to detect the occurrence of a step taken by the patient based on the rectified signal.

2. The device of claim 1, wherein the rectified signal comprises a sequence of rectification values each having a calculated value of zero or a non-zero positive value.

3. The device of claim 1, wherein a spacing in time between a first current value of the output signal associated with a first window and a second current value of the output signal associated with a second window of the plurality of moving windows is determined by a sample rate used to sample the output signal.

4. The device of claim 1, wherein the processing circuitry sequence the rectified values from each of the plurality of moving windows in order over time to generate the rectified signal.

5. The device of claim 1, wherein the output signal comprise a series of sample values of a raw signal provided by the accelerometer, and wherein each one of the plurality of moving windows is configured use a single one of the sample values of the output signal as the current value associated with the window.

6. The device of claim 5, wherein each of the plurality of moving windows encloses a predetermined number of sample values of the series of sample values.

7. The device of claim 1, wherein to analyze the rectified signal to detect a step, the processing circuitry is configured to:
  detect that the rectified signal has reached a peak value,
  set an initial threshold value and a rate for decreasing the threshold value based on the amplitude of the peak value,
  determine that the peak value has returned to a baseline value and is below a threshold floor value,
  begin decreasing the threshold value from the initial value at the rate determined for decreasing the threshold value until the threshold value is either equal to the threshold floor value or to the value of the rectified signal, and
  detect the occurrence of a step when the threshold value equals the value of the rectified signal and the value of the rectified signal is above the threshold floor value.

8. The device of claim 1, wherein the processing circuitry is configured receive an indication from the step sensor circuit that a step has been detected, and increment a counter value stored in the counter if a minimum number of consecutive steps have been previously detected by the step sensor circuit within a predetermined range of time limits.

9. The device of claim 1, wherein the single axis of movement of the patient comprises a sagittal axis relative to the patient.

10. A method comprising:
  receiving, at a processing circuitry, a signal generated as an output signal from a single axis of an accelerometer, the output signal indicted of variations in accelerations along a single axis of movement of a patient;
  rectifying, using the processing circuitry, the output signal to generate a rectified signal, wherein rectifying the output signal comprises generating a rectified value for each of a plurality of moving windows imposed over the output signal by determining a current value of the output signal for the window, determining a maximum value for a portion of the output signal enclosed by the window, and subtracting the current value from the maximum value; and
  analyzing, using the processing circuitry, the rectified signal to detect the occurrence of a step taken by a patient coupled to the accelerometer.

11. The method of claim 10, wherein the generating the rectified signal comprises generating the rectified signal based on a sequence of the rectified values from each of the plurality of moving windows having a calculated value of zero or a non-zero positive value.

12. The method of claim 10, further comprising determining a spacing in time between a first current value of the output signal associated with a first window and a second current value of the output signal associated with a second window of the plurality of moving windows based on a sample rate used to sample the output signal.

13. The method of claim 10, wherein generating the rectified signal further comprises sequencing the rectified values from each of the plurality of moving windows in order over time.

14. The method of any of claim 10, wherein receiving the signal generated as an output signal further comprises:
  sampling the output signal at a predetermined sample rate to generate a series of sample values, wherein each one of the plurality of moving windows is configured use a single one of the sample values of the output signal as the current value associated with the window.

15. The method of claim 14, wherein each of the plurality of moving windows encloses a predetermined number of sample values of the series of sample values.

16. The method of claim 10, wherein analyzing the rectified signal to detect the occurrence of the step taken by the patient further comprises:
  detecting that the rectified signal has reached a peak value,
  setting an initial threshold value and a rate for decreasing for a threshold value based on an amplitude of the peak value,
  determining that the peak value has returned to a baseline value and is below a threshold floor value,
  begin decreasing the threshold value from the initial threshold value at the rate determined for decreasing the threshold value until the threshold value is either equal to the threshold floor value or to the value of the rectified signal, and
  detecting the occurrence of a step when the threshold value equals the value of the rectified signal and the value of the rectified signal is above the threshold floor value.

17. The method of claim 10, wherein analyzing the rectified signal to detect the occurrence of a step taken by a patient further comprises:
  determining an elapsed time period between an indication of the detection of a step and the time when the previously detected step was detected;
  determining if the elapsed time period falls within a time range defined by an upper and a lower time limit, and
  if the elapsed time falls within the time range, incrementing a counter value stored in a counter used to track a number of detected steps.

18. The method of claim 17, wherein the time range is from 0.33 seconds to 2.0 seconds.

19. The method of claim 10, wherein the single axis of movement comprises a sagittal axis relative to the patient coupled to the accelerometer.

20. A step detection and tracking system comprising:
  an implantable medical device, the implantable medical device comprising:
    an accelerometer circuitry configured to output a signal indicative of variations in accelerations along a single axis of movement of patient; and
    processing circuitry configured to:
      receive the output signal from the accelerometer, and to rectify the output signal to generate a rectified signal,
      wherein rectification of the output signal comprises generating a rectified value for each of a plurality of moving windows imposed over the output signal, wherein generating the rectification value for each of the plurality of moving windows comprises determining a current value of the output signal for the window, determining a maximum value for a portion of the output signal enclosed by the window, and subtracting the current value from the maximum value, and
analyze the rectified signal to detect the occurrence of a step taken by a patient based on the rectified signal; and an external device communicatively coupled to the implantable medical device, the external device comprising a display having at least one display field configured to display an indication of a number of steps detected by the implantable medical device.

* * * * *